(12) United States Patent
Akaki

(10) Patent No.: US 8,046,707 B2
(45) Date of Patent: Oct. 25, 2011

(54) MEDICAL IMAGING APPARATUS WHICH DISPLAYS PREDETERMINED INFORMATION IN DIFFERENTIABLE MANNER FROM OTHERS

(75) Inventor: Kazuya Akaki, Tochigi-Ken (JP)

(73) Assignees: Kabushiki Kaisha Toshiba, Tokyo (JP); Toshiba Medical Systems Corp., Otawara-shi (JP)

( * ) Notice: Subject to any disclaimer, the term of this patent is extended or adjusted under 35 U.S.C. 154(b) by 842 days.

(21) Appl. No.: 10/745,695

(22) Filed: Dec. 29, 2003

(65) Prior Publication Data

US 2004/0207661 A1   Oct. 21, 2004

(30) Foreign Application Priority Data

Dec. 27, 2002 (JP) .................................. 2002-380476

(51) Int. Cl.
*G06F 3/048* (2006.01)
(52) U.S. Cl. ...................... 715/767; 715/761; 715/764
(58) Field of Classification Search .......... 382/128–134, 382/154; 600/439; 715/764, 761, 767
See application file for complete search history.

(56) References Cited

U.S. PATENT DOCUMENTS

| | | | | |
|---|---|---|---|---|
| 3,939,697 A | * | 2/1976 | Lund et al. ...................... 73/614 |
| 5,230,623 A | * | 7/1993 | Guthrie et al. .................. 433/72 |
| 5,325,481 A | * | 6/1994 | Hunt .............................. 715/809 |
| 5,383,454 A | * | 1/1995 | Bucholz ........................ 600/429 |
| 5,413,106 A | * | 5/1995 | Fujita et al. ................... 600/443 |
| 5,452,416 A | * | 9/1995 | Hilton et al. .................. 715/783 |
| 5,473,536 A | * | 12/1995 | Wimmer ......................... 700/90 |
| 5,558,091 A | * | 9/1996 | Acker et al. .................. 600/424 |
| 5,579,462 A | * | 11/1996 | Barber et al. ................. 345/440 |
| 5,661,816 A | * | 8/1997 | Fantone et al. ............... 382/100 |
| 5,662,111 A | * | 9/1997 | Cosman ........................ 600/417 |
| 5,682,526 A | * | 10/1997 | Smokoff et al. ........... 707/104.1 |
| 5,848,967 A | * | 12/1998 | Cosman ........................ 600/426 |
| 5,896,131 A | * | 4/1999 | Alexander .................... 345/634 |
| 5,922,018 A | * | 7/1999 | Sarvazyan .................... 600/587 |
| 5,953,009 A | * | 9/1999 | Alexander .................... 715/771 |
| 5,956,013 A | * | 9/1999 | Raj et al. ...................... 345/208 |
| 5,961,462 A | * | 10/1999 | Loupas et al. ................ 600/453 |
| 5,986,662 A | * | 11/1999 | Argiro et al. ................. 345/424 |
| 5,987,349 A | * | 11/1999 | Schulz ......................... 600/427 |
| 6,001,061 A | * | 12/1999 | Ogishima et al. ............ 600/440 |
| 6,006,126 A | * | 12/1999 | Cosman ........................ 600/426 |
| 6,157,855 A | * | 12/2000 | Sjoholm ....................... 600/427 |
| 6,167,295 A | * | 12/2000 | Cosman ........................ 600/426 |
| 6,192,164 B1 | * | 2/2001 | Park ............................. 382/300 |
| 6,219,059 B1 | * | 4/2001 | Argiro ......................... 345/424 |

(Continued)

FOREIGN PATENT DOCUMENTS

JP             09327457 A  * 12/1997

(Continued)

*Primary Examiner* — Weilun Lo
*Assistant Examiner* — Eric Wiener
(74) *Attorney, Agent, or Firm* — Oblon, Spivak, McClelland, Maier & Neustadt, L.L.P.

(57) ABSTRACT

A medical imaging apparatus for generating medical information includes an input unit, a processor, and a display. The input unit is operated by a user and is configured to input an instruction. The processor is configured to process a first part of display information relating to the medical information based on the instruction so that the first part is displayed in a differentiable manner from others of the display information. The display is configured to display the processed first part and the others of the display information.

44 Claims, 21 Drawing Sheets

U.S. PATENT DOCUMENTS

| | | | |
|---|---|---|---|
| 6,248,074 B1 * | 6/2001 | Ohno et al. | 600/463 |
| 6,266,453 B1 * | 7/2001 | Hibbard et al. | 382/294 |
| 6,275,725 B1 * | 8/2001 | Cosman | 600/426 |
| 6,306,089 B1 * | 10/2001 | Coleman et al. | 600/437 |
| 6,351,661 B1 * | 2/2002 | Cosman | 600/426 |
| 6,366,799 B1 * | 4/2002 | Acker et al. | 600/424 |
| 6,409,686 B1 * | 6/2002 | Guthrie et al. | 600/587 |
| 6,411,299 B1 * | 6/2002 | Stoval et al. | 345/467 |
| 6,454,712 B1 * | 9/2002 | Oonuki | 600/437 |
| 6,468,212 B1 * | 10/2002 | Scott et al. | 600/437 |
| 6,500,118 B1 * | 12/2002 | Hashimoto | 600/437 |
| 6,544,041 B1 * | 4/2003 | Damadian | 434/262 |
| 6,574,498 B1 * | 6/2003 | Gilboa | 600/424 |
| 6,577,753 B2 * | 6/2003 | Ogawa | 382/132 |
| 6,593,884 B1 * | 7/2003 | Gilboa et al. | 342/448 |
| 6,607,518 B1 * | 8/2003 | Hazeleger | 604/515 |
| 6,675,038 B2 * | 1/2004 | Cupples et al. | 600/424 |
| 6,685,637 B1 * | 2/2004 | Rom | 600/437 |
| 6,714,883 B1 * | 3/2004 | Samuels | 702/68 |
| 6,740,039 B1 * | 5/2004 | Rafter et al. | 600/439 |
| 6,793,625 B2 * | 9/2004 | Cavallaro et al. | 600/440 |
| 6,907,366 B2 * | 6/2005 | Iiyoshi et al. | 702/68 |
| 6,937,237 B2 * | 8/2005 | McCarthy et al. | 345/440 |
| 6,944,330 B2 * | 9/2005 | Novak et al. | 382/162 |
| 6,947,788 B2 * | 9/2005 | Gilboa et al. | 600/435 |
| 6,954,767 B1 * | 10/2005 | Kanada | 1/1 |
| 7,006,955 B2 * | 2/2006 | Daft et al. | 703/5 |
| 7,106,479 B2 * | 9/2006 | Roy et al. | 358/3.27 |
| 7,209,578 B2 * | 4/2007 | Saito et al. | 382/128 |
| 2001/0047133 A1 * | 11/2001 | Gilboa et al. | 600/429 |
| 2002/0005719 A1 * | 1/2002 | Gilboa et al. | 324/309 |

FOREIGN PATENT DOCUMENTS

| | | | |
|---|---|---|---|
| JP | 10-328179 | | 12/1998 |
| JP | 2000135216 A | * | 5/2000 |
| JP | 2000-259747 | | 9/2000 |
| JP | 2001-061836 | | 3/2001 |
| JP | 2001061836 A | * | 3/2001 |
| JP | 2001224596 A | * | 8/2001 |
| JP | 2002-282250 | | 10/2002 |
| JP | 2002-336254 | | 11/2002 |

* cited by examiner

FIG. 12

TOSHIBA 1234512345:— 0  
TOSHIBA  — OPE - Adult Heart  2002/09/26  4:38:14PM Cardiac ▶

The report shows averaged value. Check all data.    Averaged

LV (M)

Teichholz

| | | | | | |
|---|---|---|---|---|---|
| EDV | 85.8 | mL | EF | 63.4 | % |
| ESV | 31.4 | mL | FS | 34.2 | % |
| SV | 54.4 | mL | | | |

| | | | | | |
|---|---|---|---|---|---|
| IVSTd | 13.6 | mm | IVSTs | 14.8 | mm |
| LVIDd | 43.6 | mm | LVIDs | 28.7 | mm |
| LVPWTd | 8.5 | mm | LVPWTs | 12.6 | mm |

LV Mass(M)

AV Cube

| | | | | | |
|---|---|---|---|---|---|
| LV MASSd | 168 | g | LV MASSs | 128 | g |

| Abdomen 1 | Abdomen 2 | Abdomen 3 | Abdomen 4 | Abdomen 5 | Abdomen 6 | Abdomen 7 |

| Liver | GB | Pancreas | R-Kidney | | Size | Small |
| Spleen | CBD | PD | L-Kidney | | | |
| SOL | Stone | Polyp | Cyst | | | |
| Ascites | Prostate | Ut | Bladder | | All Delete | |
| ↙ | ← | ↖ | ↑ | | Delete | |
| ↘ | → | ↗ | ↓ | | Set Home | |

| 0 | 8 | 3 | 60 | -10 | 2.0 | H | +10 | 8 | 8 |

1800

MEDICAL IMAGING APPARATUS WHICH DISPLAYS PREDETERMINED INFORMATION IN DIFFERENTIABLE MANNER FROM OTHERS

CROSS-REFERENCE TO RELATED APPLICATION

This application is based upon and claims the benefit of priority from prior Japanese Patent Application No. P2002-380476, filed on Dec. 27, 2002, the entire contents of which are incorporated herein by reference.

BACKGROUND OF THE INVENTION

1. Field of the invention

The present invention relates to a medical imaging apparatus and a medical information processing apparatus, each of which is operative, based on an instruction given by a user, to process and display the medical information. The present invention further relates to a method of such processing and display based on the instruction.

2. Discussion of the Background

Various types of medical image diagnosis apparatuses are used for medical examinations so as to obtain information inside a patient's body. One type of such an apparatus is an ultrasound diagnosis apparatus. In the ultrasound diagnosis apparatus, so-called B mode images and so-called M mode images are often produced and used for various medical diagnoses. The B mode image is a tissue tomogram of soft tissues inside the patient's body, produced in an ultrasound reflection method. The M mode image is an image aligning tissue images in parallel included in a line of the tissue tomogram in time series. By referring to the M mode image, a doctor or other user of the ultrasound diagnosis apparatus (hereinafter referred to as a user) can observe a morphological variation over time of a heart, blood vessels, and the like in detail.

An ultrasound diagnosis apparatus implementing such diagnoses mentioned above, has some advantages in the following aspects, compared to an X-ray diagnosis apparatus, an X-ray computed tomography, a magnetic resonance imaging apparatus, and a nuclear medicine diagnosis apparatus such as a SPECT and a PET. For, example, the user can easily observe a motion of a heart or a fetus in real time by touching an ultrasonic probe on a body surface of the patient. In addition, the user can obtain a spectrum or a spatial spread of blood flow through a Doppler effect. Further, an ultrasound causes very little harm to a human body, and so it is possible to repeat examinations with an ultrasound. Still further, an ultrasound diagnosis apparatus is very compact in size, and so an examination can be made with the apparatus placed at bed side. Therefore, an ultrasound diagnosis apparatus is widely used for medical examinations including those for a heart, an abdomen, a mammary gland, a urinary organ, and obstetrics.

A lot of ultrasound diagnosis apparatuses are regularly or optionally equipped with an application program for measuring structural sizes of a distance, an area, a volume, and the like of various tissues based on a B mode image, and also for measuring a variation over time based on an M mode image. Measurement results and calculation results from such measurements are not only displayed but can also be edited freely in a worksheet. The edited results can finally be output as a report. This is, for example, introduced in Japanese Patent Application Publication Nos. 2001-61836 and 2002-282250.

Further, the above-mentioned measurements may be implemented in an ultrasound image processing apparatus having a similar application program. The ultrasound image processing apparatus is connected to and receives ultrasound images from the ultrasound diagnosis apparatus. Accordingly, such measurements can be realized even in a remote place.

Recently, measurement functions have been specialized for each purpose of, for example, circulatory organ diagnosis and fetus diagnosis. This specialization results in a great number of measurement parameters and calculation parameters. Further, a lot of authors are present with respect to calculation techniques of the calculation parameters. Usability and significance are different among these calculation techniques. Therefore, the selection of a calculation technique is left entirely up to the user.

Under this situation, however, a lot of measurement parameters and calculation parameters are displayed in an operation panel. This leads to a problem of requiring the user to spend time to find desired measurement parameters in the display. Further, since a lot of measured data and calculated data are displayed in a display monitor, there is a problem that the user must spend time to find desired or interesting data from among the displayed measured data and calculated data. Still further, there are displayed a plurality of measuring calipers which are used for designating a point or a range to be measured in the display monitor. Therefore, it is a problem for the user to take time to recognize which measurement caliper the desired or interesting measured data and calculated data are based.

SUMMARY OF THE INVENTION

According to a first aspect of the present invention, there is provided a medical imaging apparatus for generating medical information. The apparatus includes an input unit, a processor, and a display. The input unit is operated by a user and is configured to input an instruction. The processor is configured to process a first part of display information relating to the medical information based on the instruction so that the first part is displayed in a differentiable manner from others of the display information. The display is configured to display the processed first part and other display information.

According to a second aspect of the present invention, there is provided a medical information processing apparatus for processing medical information generated in a medical imaging equipment. The apparatus includes a receiver, an input unit, and a processor. The receiver is configured to receive the medical information. The input unit is operated by a user and is configured to input an instruction. The processor is configured to process a first part of display information relating to the medical information based on the instruction so that the first part is displayed in a differentiable manner from others of the display information. The processor is further configured to output the processed first part and other display information.

According to a third aspect of the present invention, there is provided a method of processing medical information generated in a medical imaging equipment. The method begins by receiving an instruction input by a user. The method continues by processing a first part of display information relating to the medical information based on the instruction so that the first part is displayed in a differentiable manner from others of the display information. The method further continues by displaying the processed first part and other display information.

According to a fourth aspect of the present invention, there is provided a computer program product on which is stored a computer program for processing medical information generated in a medical imaging equipment. The computer program has instructions, which when executed, perform steps comprising determining an instruction input by a user, and processing a first part of display information relating to the medical information based on the instruction so that the first part is displayed in a differentiable manner from other display information.

BRIEF DESCRIPTION OF THE DRAWINGS

A more complete appreciation of embodiments of the present invention and many of its attendant advantages will be readily obtained by reference to the following detailed description considered in connection with the accompanying drawings, in which:

FIG. 12 is an illustration showing a second example of the report to be output or transmitted according to the fourth embodiment of the present invention;

FIG. 17 is an illustration showing a first exemplary display of the touch command screen according to an eighth embodiment of the present invention;

FIG. 18 is an illustration showing a second exemplary display of the touch command screen according to the eighth embodiment of the present invention;

DESCRIPTION OF THE PREFERRED EMBODIMENTS

Embodiments of the present invention will be described with reference to the accompanying drawings. In the following embodiments of the present invention an ultrasound diagnosis apparatus will be described only as an example of a medical imaging apparatus. The embodiments of the present invention can also be applied to other medical imaging apparatuses including, but not limited to, an X-ray diagnosis apparatus, an X-ray computed tomography apparatus, a magnetic resonance imaging apparatus, a nuclear medicine diagnosis apparatus, and an endoscope.

Figure 1:
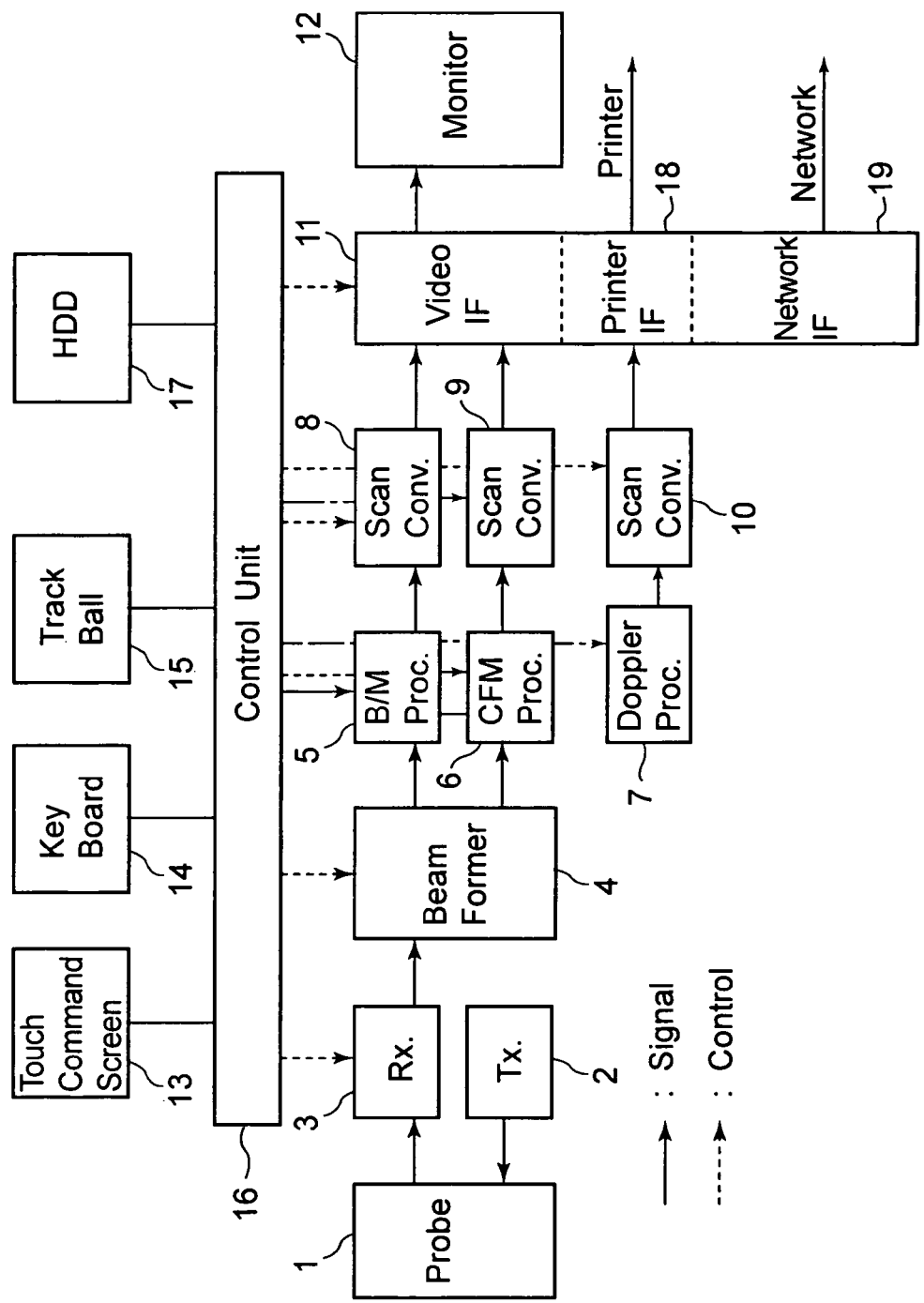
FIG. 1 is a block diagram showing an exemplary configuration of an ultrasound diagnosis apparatus according to embodiments of the present invention.

FIG. 1 is a block diagram showing an exemplary configuration of an ultrasound diagnosis apparatus according to the embodiments of the present invention. As shown in FIG. 1, an ultrasonic probe 1 receives driving pulses from a transmitter 2 and transmits an ultrasound to within a body of an object or a patient. An ultrasound returning from the patient's body as a reflection and a scatter is received by the ultrasonic probe 1. Very small electrical signals are output from each of a plurality of elements included in the ultrasonic probe 1 and are amplified by a receiver 3. A beam former 4 is a reception signal analog to digital (A/D) converter and converts the amplified signals into digital signals. The digital signals are given an appropriate delay and added to one another in a phase-adjusted manner for the focusing among the elements.

Focused signals are processed in a B mode and M mode processor (hereinafter referred to as a B/M mode processor) 5 and a CFM (color flow mapping) mode processor 6 as appropriately for the modes, respectively Usually, in the B/M mode processor 5 the focused signals are band-pass filtered and an envelope component of the filtered signals is detected. Further, the detected envelope component is compressed logarithmically. On the other hand, the CFM mode processor 6 implements a high-pass filtering processing, such as a MTI (moving target indicator) filtering and a Wall filtering, for separating tissue signals from blood flow signals.

A Doppler processor 7 is an autocorrelation processing unit, and implements an autocorrelation processing for detecting a moving speed of blood flows and tissues. In the Doppler processor 7, a nonlinear processing may also be implemented for reducing or removing the tissue signals. The signals processed in the B/M mode processor 5 are input to a scan converter 8. The signals processed in the CFM mode processor 6 are input to a scan converter 9. The signals processed in the Doppler processor 7 are input to a scan converter 10. In each of the scan converters 8-10, the input signals are mapped to positions corresponding to the transmission and the reception of the ultrasound beam, respectively. The mapped signals are output to a video interface 11 from each of the scan converters 8-10. Finally, ultrasound images corresponding to the mode are displayed based on the mapped signals in a monitor 12.

When the ultrasound images are displayed in the monitor 12, the user operates a touch command screen 13, a keyboard 14, and/or a track ball 15 for various measurements on an objective part of the displayed ultrasound images. The various measurements include a measurement of a distance and a measurement of a blood flow speed. In response, a control unit 16 implements various measurements in accordance with the user's operation. The control unit 16 causes the measurement results and calculation results calculated based on the measurement results to be displayed in the monitor 12. The control unit 16 implements displaying controls over the monitor 12 and the touch command screen 13.

When the user operates the touch command screen 13, the keyboard 14, and/or the track ball 15 to differentiate specific one or more of various measurement parameters and calculation parameters displayed in the touch command screen 13 (or the monitor 12), the control unit 16 controls in response to the user's operation and causes the specific one or more measurement parameters and/or calculation parameters to be displayed in a differentiable manner from other measurement parameters and calculation parameters. Here, the 'parameters' indicate parameter items (or names) and/or values, as necessary. Information regarding possible differentiable manner of measurement parameters and/or calculation parameters is stored in a hard disk drive (HDD) 17. Accordingly, the control unit 16 implements differentiating processing on specific (or designated) parameters in accordance with the differentiable manner stored in the hard disk drive 17.

The ultrasound diagnosis apparatus further includes a printer interface 18 and a network interface 19. Instead of, or in addition to the display in the monitor 12 through the video interface 11, the mapped signals output from one or more of the scan converters 8-10 are input to the printer interface 18 and/or the network interface 19. Accordingly, the ultrasound images based on the mapped signals can be output to an external printer and printed out. Similarly, the ultrasound images based on the mapped signals can also be output to a network and used for various purposes.

Figure 2:
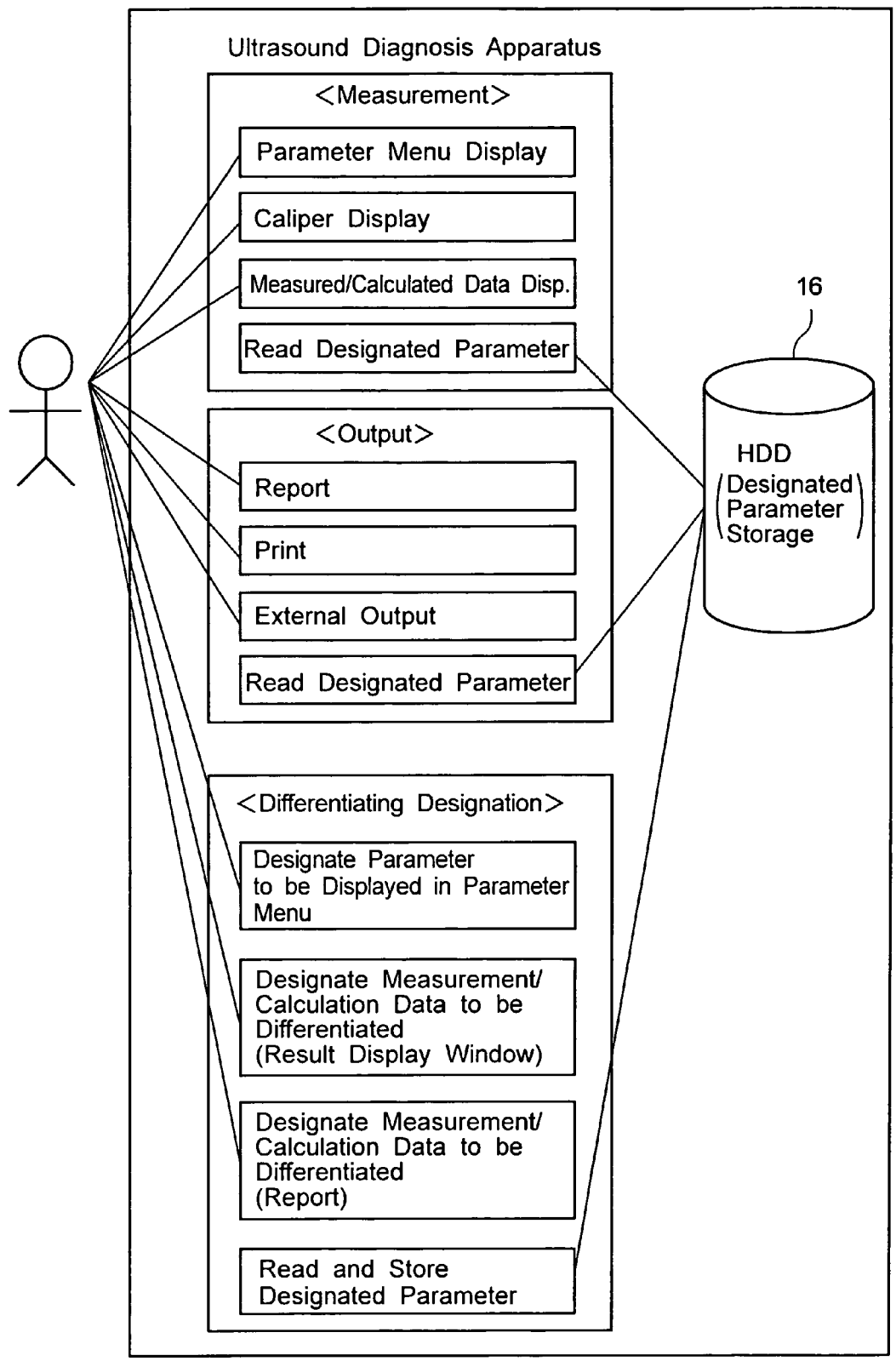
FIG. 2 is an illustration showing an example of a use case representing a software configuration installed in the ultrasound diagnosis apparatus according to embodiments of the present invention.

FIG. 2 is an illustration showing an example of a use case representing a software configuration installed in the ultrasound diagnosis apparatus according to the embodiments of the present invention.

The ultrasound diagnosis apparatus incorporates an application program for measurements. The application program realizes, for example, a measurement of a structural size, such as a distance, an area, and a volume of various tissues based on B mode images. The application program also realizes, for example, a measurement of temporal variation based on M mode images. As shown in FIG. 2, the application program installed in the ultrasound diagnosis apparatus includes a measurement function, output function, and differentiating designation function.

When the user performs an ultrasound diagnosis, the user may first use a measurement function so as to measure and calculate various parameters. Next, the user may use an output function to output a result of the measurement and calculation on paper or to an external apparatus. In addition, however, when the user prefers to see specific one or more parameters in a differentiable manner from other parameters in the monitor 12 and/or the touch command screen 13 during a use of the above functions, the user can use a parameter differentiating designation function in advance of or during the use of the measurement or the output function so as to designate desired parameters to be displayed in a differentiable manner.

Selecting one of the functions including the above three functions is, for example, accomplished by user's using the keyboard 14 or the track ball 15 for a GUI (graphical user interface) menu displayed in the monitor 12. Alternatively, for example, the user may touch and select a desired function item in a function selecting view displayed in the touch command screen 13.

Each of the above three functions will be described in detail along an example of an ultrasound diagnosis flow.

When the user selects the measurement function so as to perform various measurements, the measurements will mainly be implemented in accordance with the following phases. In the following description, various display controls, measurements, and calculations of data in the monitor 12 and the touch command screen 13 may be computed and processed in the control unit 17.

(1) Measurement Parameter Selection

The user selects measurement parameters in measurement implementation from a GUI menu in the monitor 12 or from a selection view in the touch command screen 13.

(2) Measurement Caliper Setting

In response to the above selection, a measurement caliper corresponding to the selected parameters is displayed on an ultrasound image in the monitor 12. The measurement caliper is a GUI for designating a position or a range of a measurement object. The user sets the measurement caliper at a place of the measurement object in the ultrasound image.

(3) Measured Data Display and Calculated Data Display

In response to the measurement caliper setting, various measured data corresponding to the place of the measurement caliper are displayed in a measured value display area in the monitor 12. The various measured data represent measurement parameters. Further, various calculated data obtained by calculation based on the various measured data are also displayed in the measured value display area in the monitor 12. The various calculated data represent calculation parameter names, calculated values, and the like, if any.

Figure 3:
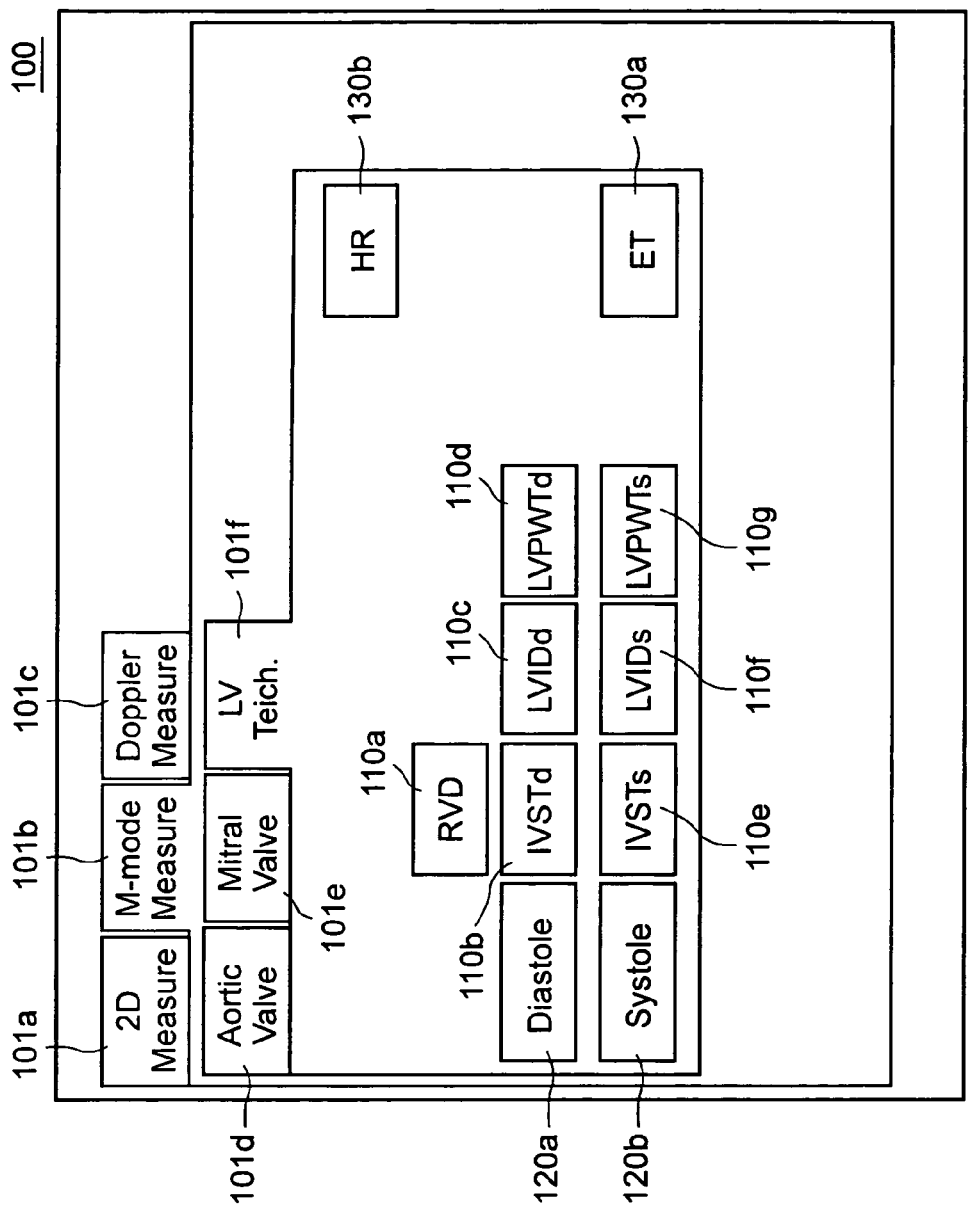
FIG. 3 is an illustration showing an exemplary display of a touch command screen according to the embodiments of the present invention.

In more detail, when the user selects the measurement function, a measurement parameter selection menu, for example measurement parameter selection menu 100, is displayed in the touch command screen 13 as shown in FIG. 3. FIG. 3 is an illustration showing an exemplary display of the touch command screen 13 according to embodiments of the present invention. When measurement parameters are displayed in the measurement parameter selection menu 100, the control unit 16 reads out parameters to be differentiated and a differentiating manner from the hard disk drive 17. The control unit 16 causes the measurement parameters to be displayed in a differentiable manner according to the read-out differentiating manner (See FIG. 5, for example). The user selects desired measurement parameters by touching one or more parameters in the measurement parameter selection menu 100. Alternatively, the user operates the keyboard 14 or the track ball 15 so that a GUI menu is displayed in the monitor 12. The user can select the desired measurement parameters in the displayed GUI menu. Accordingly, a measurement screen corresponding to the selected measurement parameters is displayed in the monitor 12 (See FIG. 4, for example). In the measurement screen, measurement calipers are displayed in an ultrasound image display area. Also, measured data and calculated data based on the measurement calipers are displayed in a measured value display area. For this display, the control unit 16 reads out parameters to be differentiated and a differentiating manner from the hard disk drive 17. The control unit 16 causes the parameters to be displayed in a differentiable manner according to the read-out differentiating manner (See FIG. 7, for example).

Figure 11:
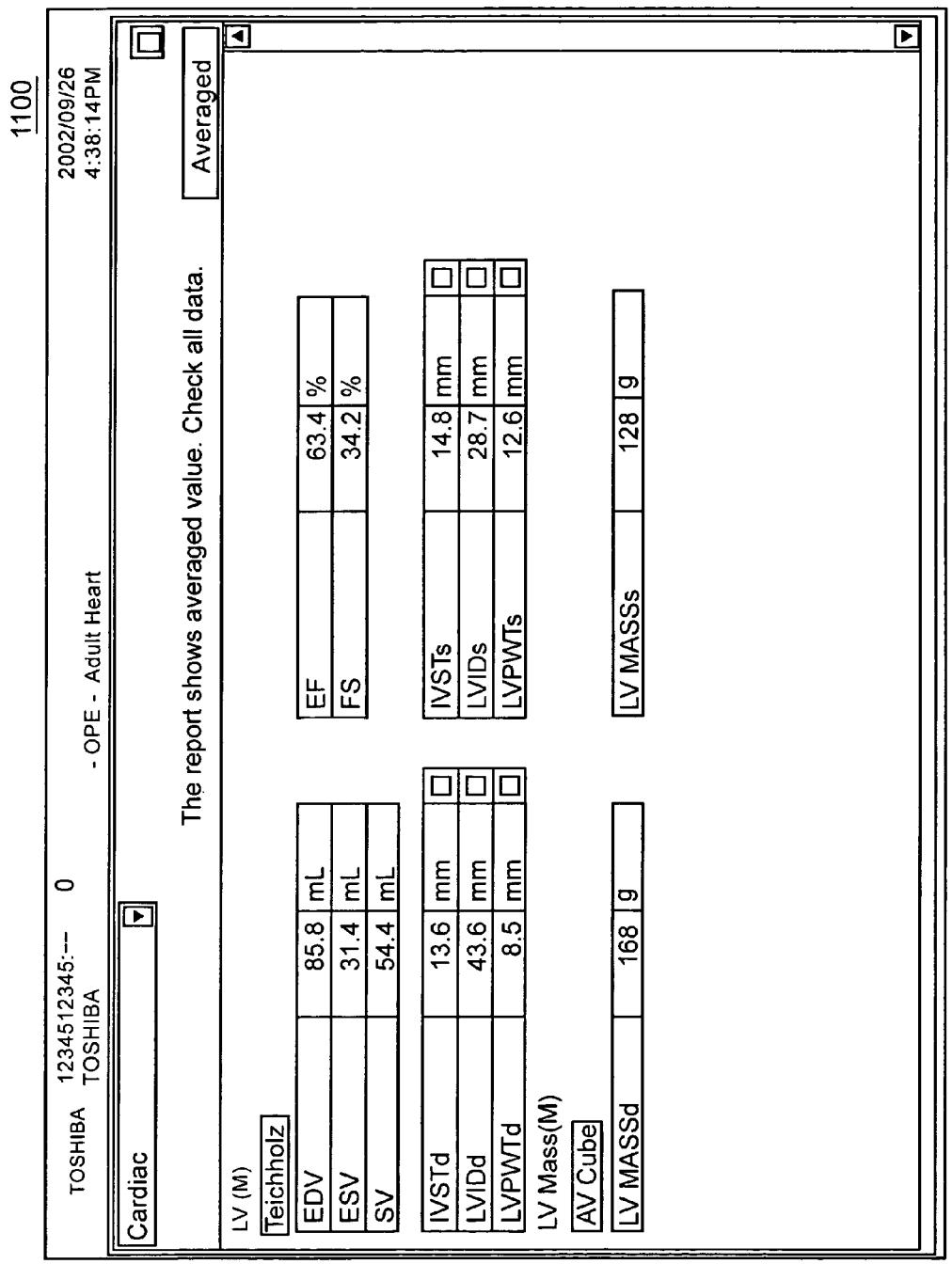
FIG. 11 is an illustration showing a first example of a report to be output or transmitted according to a fourth embodiment of the present invention.

After the measurements and the calculations by the measurement function, when the user selects the output function for outputting the measurement result and the calculation results on a paper or to an external apparatus, a report showing a list of various measurement results and calculation results is displayed in the monitor 12 (See FIG. 11, for example). When the measurement results and the calculation results are displayed in the report, the control unit 16 reads out parameters to be differentiated and a differentiating manner from the hard disk drive 17. The control unit 16 causes the parameters to be displayed in a differentiable manner according to the read-out differentiating manner (See FIG. 12, for example). In this output function, a displayed content of the report can be output to a video cassette recorder, a DVD recorder, or the like through the video interface 11 in response to a user's predetermined operation with the keyboard 14 or the track ball 15. Similarly, the displayed content of the report can also be output to a printer through the printer interface 18. Further, when there is an external apparatus such as an image management server communicably connected to the ultrasound diagnosis apparatus, the displayed content of the report can also be output to the external apparatus through the network interface 19. In case the external apparatus is, for example, a DICOM (Digital Imaging and Communication for Medicine) server, the control unit 16 adds a flag for the differentiating display to the measured data and calculated data. When the measured data and calculated data with the flag are transmitted to the DICOM server, the differentiating display is realized in the DICOM server.

Figure 8:
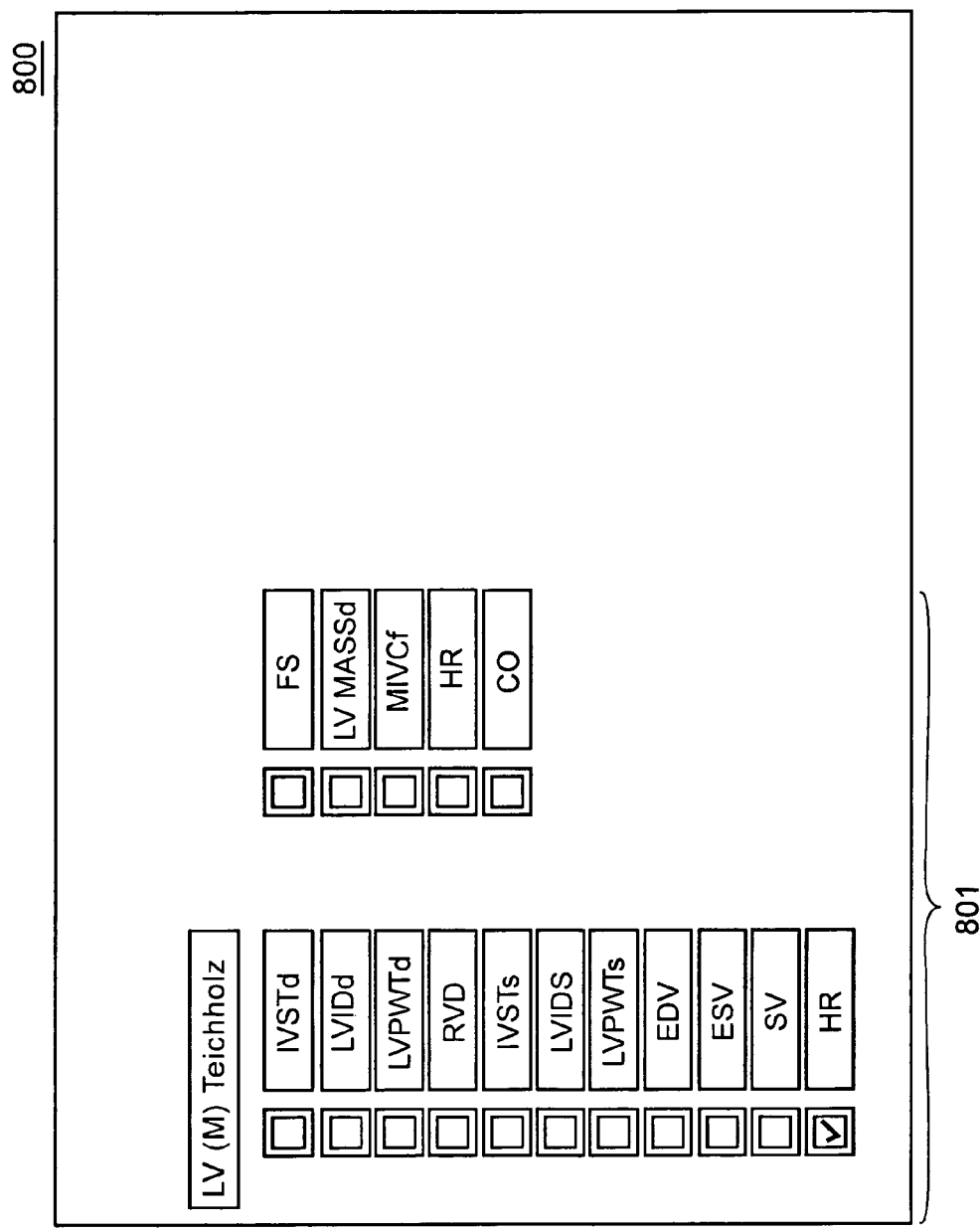
FIG. 8 is an illustration showing an example of a differentiated display parameter setting menu according to the second embodiment of the present invention.

While the user is using the measurement function or the output function, the user can select the parameter differentiating designation function in advance of or during the use of the functions so as to display one or more of the various measurement parameters, the calculation parameters, the measurement results, and the calculation results in the touch command screen 13 in a differentiable manner. In this case, for example, a differentiated display parameter setting menu is displayed in the monitor 12 (See FIG. 8, for example). In FIG. 8, various measurement parameters in a measurement function 'LV (M) Teichholz' are displayed. When the various measurement parameters are displayed in the differentiated display parameter setting menu, the control unit 16 reads out parameters to be differentiated from the hard disk drive 17. The control unit 16 controls the monitor 12 to display the read-out parameters as currently stored parameters for the differentiating display. The user operates the keyboard 14 or the trackball 15 in the differentiated display parameter setting menu so as to select desired measurement parameters to be differentiated. For example, the differentiated display parameter setting menu is prepared for setting parameters to be displayed in a differentiable manner, among parameters to be displayed in the measured value display area in the measurement screen displayed in the monitor 12 (See FIGS. 4 and 8, for example). In addition, another differentiated display parameter setting menu is prepared for setting parameters to be displayed in a differentiable manner, among various measurement parameters in the measurement parameter selection menu 100 displayed in the touch command screen 13 (See FIGS. 3, 5 and 6). Further, still another differentiated display parameter setting menu is prepared for setting measurement results and calculation results to be displayed in a differentiable manner, among various measurement results and calculation results in the report to be displayed in the monitor 12 (See FIGS. 11 and. 12, for example). Parameters that are selected or set in the above differentiated display parameter setting menu are stored in the hard disk drive 17 and are read out by the control unit 16.

First Embodiment

Measurement parameters are displayed in the measurement parameter selection menu in a differentiable manner according to a first embodiment of the present invention.

As described before, when various measurements are implemented in the measurement function, the user selects desired measurement parameters from the menu, such as measurement parameter selection menu 100 for example, that is displayed in the touch command screen 13.

An undifferentiated display example of the measurement parameter selection menu 100 is shown in FIG. 3. As shown in FIG. 3, various measurement parameters are displayed in the measurement parameter selection menu 100.

In FIG. 3, the measurement parameter selection menu 100 includes various measurement parameters in tab sheet format. First layer tabs include imaging modes. The imaging modes are, for example, a two dimensional mode measurement (i.e., B mode measurement) 101a, an M mode measurement 101b, and a Doppler mode measurement 101c. Further, second layer tabs under each of the first layer tabs (e.g., under the M mode measurement 101b in FIG. 3) include object parts of a human body. The object parts are, for example, an aortic valve 101d, a mitral valve 101e, and a left ventricle—Teichholz 101f. FIG. 3 further shows parameters when the left ventricle—Teichholz 101f is selected under the M mode measurement 101b. In general, the left ventricle—Teichholz is for measurement in the left ventricle level under the M mode imaging. Exemplary measurement parameters shown in FIG. 3 are a right ventricle diameter at end diastole (RVD) 110a, an interventricular septal thickness at end diastole (IVSTd) 110b, a left ventricle internal distance at end diastole (LVIDd) 110c, a left ventricle posterior wall thickness at end diastole (LVPWTd) 110d, an interventricular septal thickness at end systole (IVSTs) 110e, a left ventricle internal distance at end systole (LVIDS) 110f, and a left ventricle posterior wall thickness at end systole (LVPWTS) 110g. Each of these is selectable as a measurement parameter.

In addition, the left ventricle—Teichholz 101f further includes parameters of a diastole 120a, a systole 120b, an ejection time (ET) 130a, and a heart rate (HR) 130b. The diastole 120a can be selected for a continuous measurement of the RVD 110a, the IVSTd 110b, the LVIDd 110c, and the LVPWTd 110d. Similarly, the systole 120b can be selected for a continuous measurement of the IVSTs 110e, the LVIDs 110f, and the LVPWTs 110g. The ET 130a is for a measurement of an ejection time. The HR 130b is for a measurement of a heart rate.

Figure 4:
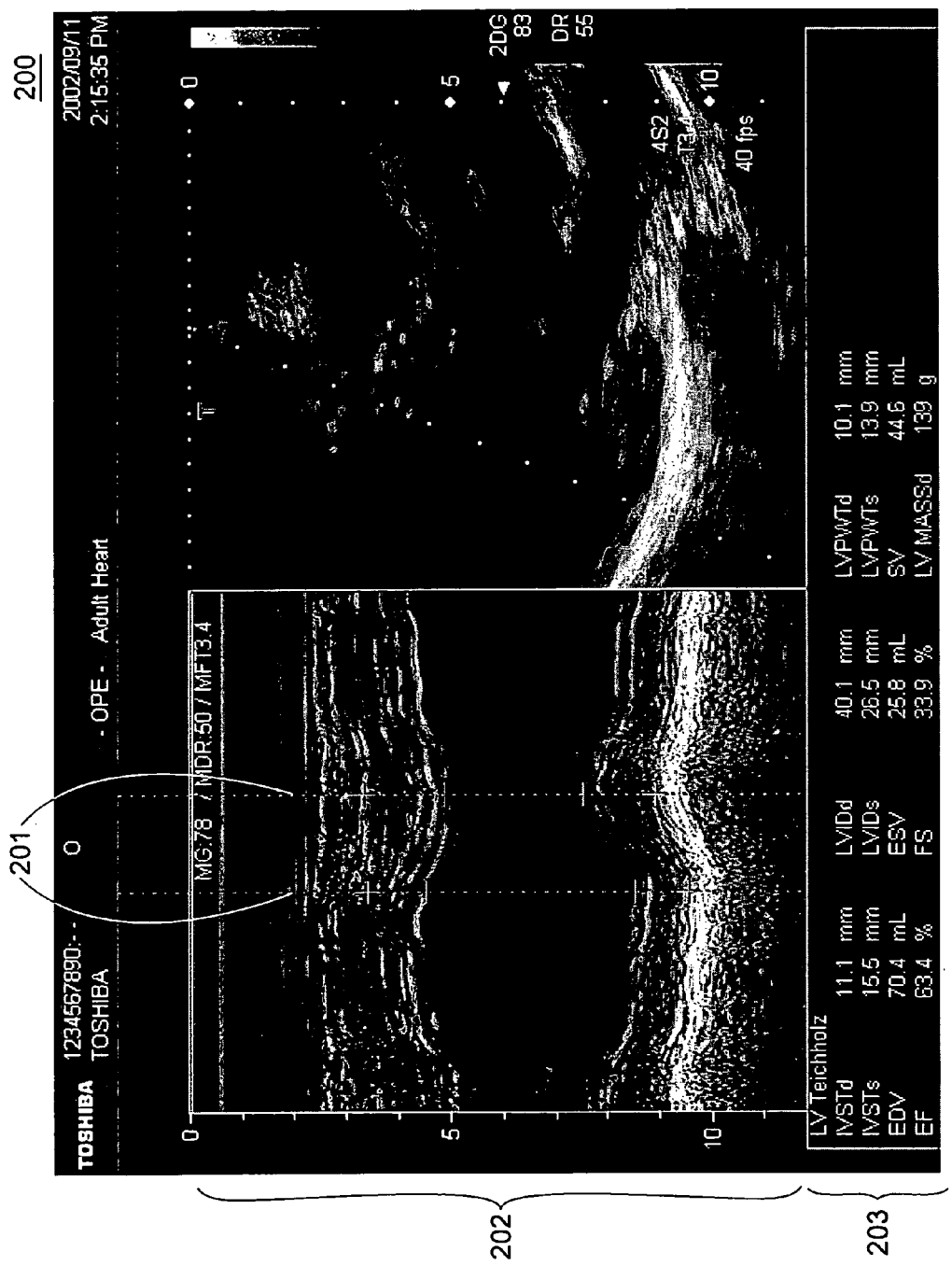
FIG. 4 is an illustration showing an undifferentiated display example according to the embodiments of the present invention.

The user selects measurement parameters which the user wants to measure among the above-mentioned parameters in the measurement parameter selection menu 100. The selection is accomplished by touching one or more desired parameters in a menu, for example, the measurement parameter selection menu 100. Accordingly, measurement calipers corresponding to the selected measurement parameters are displayed on an ultrasound image in a measurement screen 200 as shown in FIG. 4 so that the user can perform some measurements. For example, when the parameter LVIDd 110c has been selected from the measurement selection menu 100 displayed in the touch command screen 13, the control unit 16 activates measurement calipers 201 for M mode distance measurement and controls the monitor 12 to display the measurement calipers 201 on the ultrasound image in an ultrasound image display area 202 in the measurement screen 200. The user operates, for example, the trackball 15 so as to align the measurement caliper 201 with a time phase of an end diastole in the ultrasound image and to measure a left ventricle internal distance. A measurement result is displayed in a measured value display area 203 in the measurement screen 200. For example, the measurement result is displayed like 'LVIDd 40.1 mm'.

Figure 5:
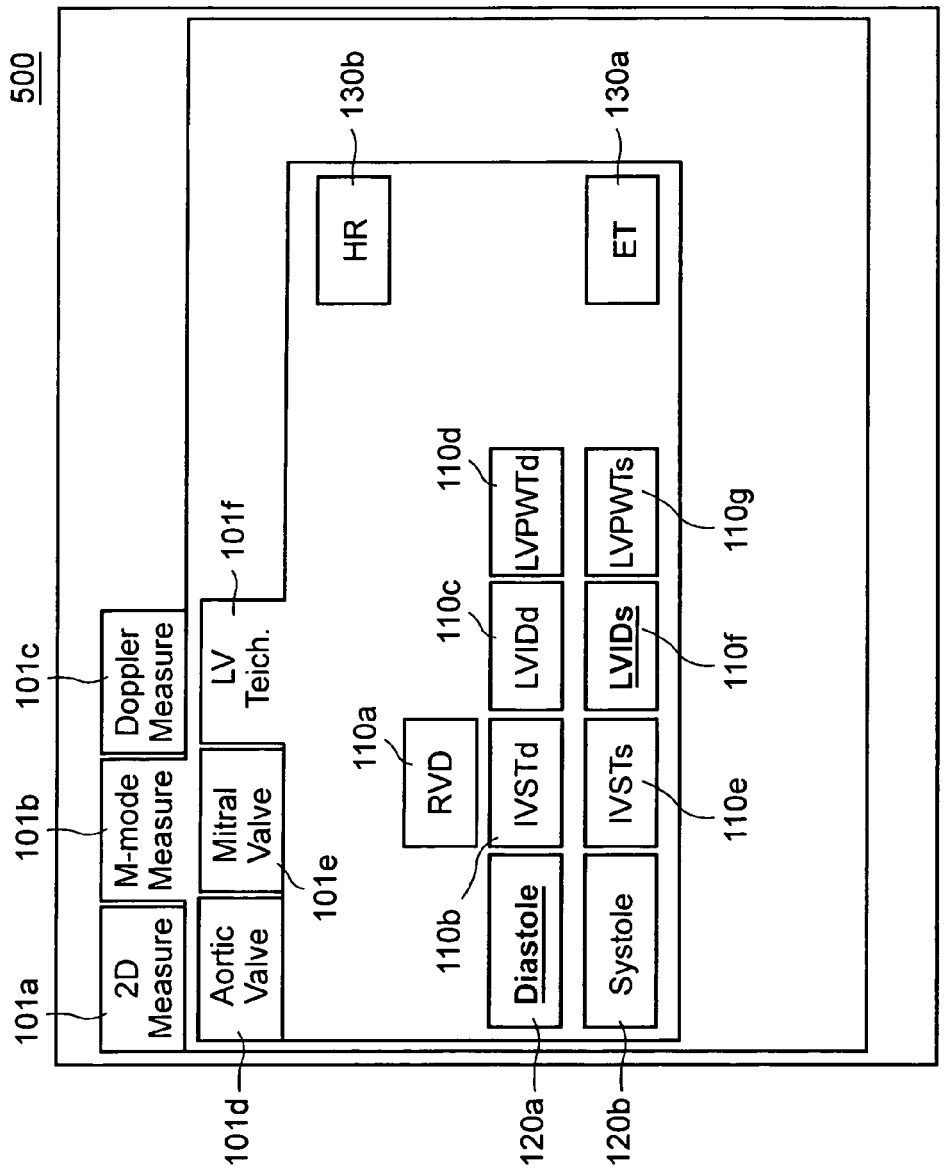
FIG. 5 is an illustration showing an exemplary display of the touch command screen according to a first embodiment of the present invention.

FIG. 5 is an illustration showing an exemplary display of the touch command screen 13 according to the first embodiment of the present invention. Some measurement parameters can be differentiated from other measurement parameters. When a measurement parameter selection menu 500 is displayed, the control unit 16 reads out parameters to be differentiated and a differentiating manner from the hard disk drive 17. The control unit 16 causes the parameters to be displayed in a differentiable manner according to the read-out differentiating manner. For example, as shown in FIG. 5, the diastole 120a and the LVIDs 110f are displayed in bold face (in a font different from others) and underlined so as to be differentiated.

Figure 6:
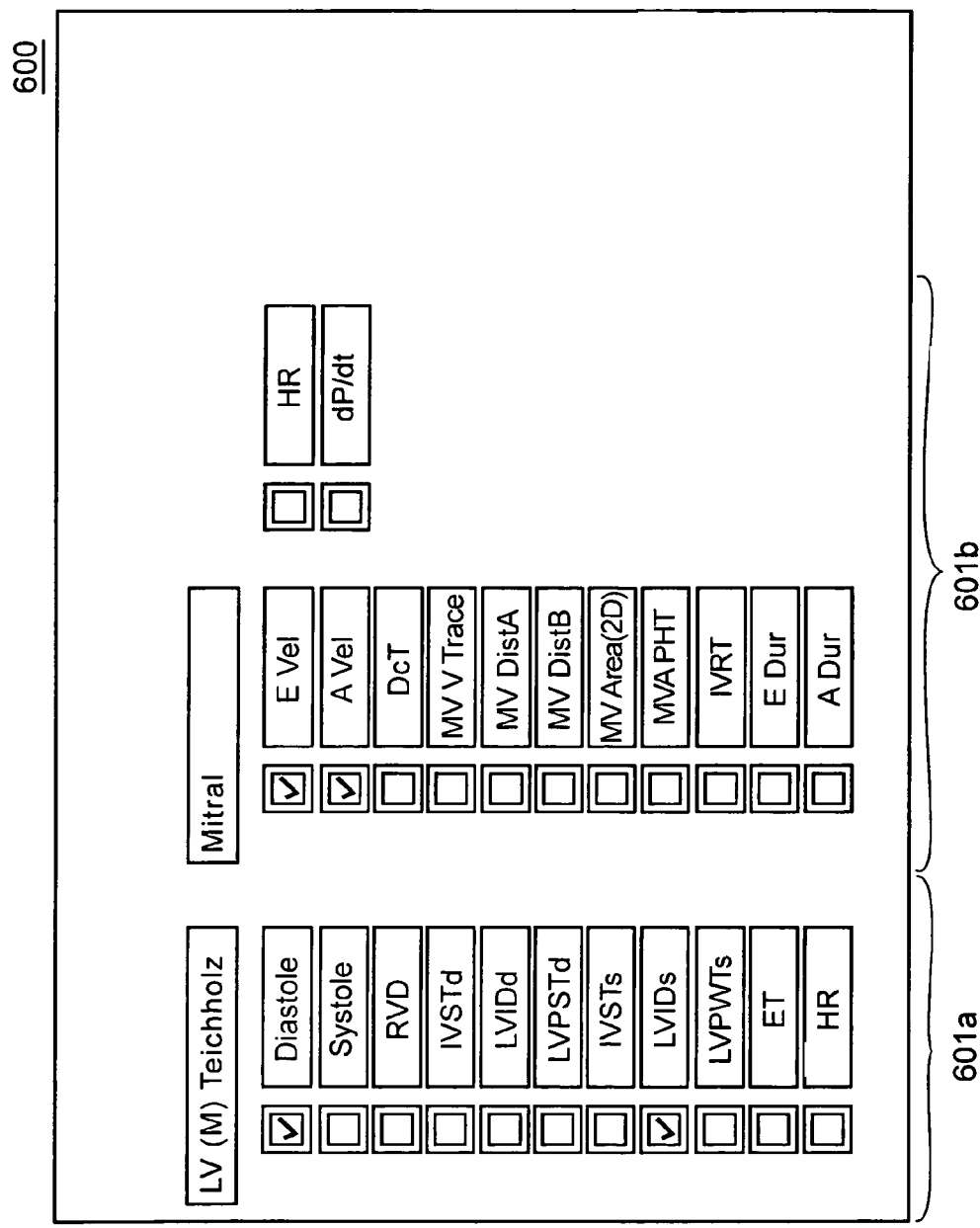
FIG. 6 is an illustration showing an example of a differentiated display parameter setting menu according to the first embodiment of the present invention.

For determining which measurement parameters are differentiated from others in the measurement parameter selection menu 500, a menu, such as differentiated display parameter setting menu 600, is used, which is shown in FIG. 6. FIG. 6 is an illustration showing an example of the differentiated display parameter setting menu according to the first embodiment of the present invention. The differentiated display parameter setting menu 600 is displayed in the monitor 12 in response to a user's predetermined operation with the keyboard 14 or the track ball 15. Referring to the differentiated display parameter setting menu 600, the user then selects desired measurement parameters to be differentiated from others. For example, in FIG. 6, measurement parameters 'Diastole' and 'LVIDs' in a measurement function 'LV (M) Teichholz') 401a are ticked for selection. This results in displaying the measurement parameters of the diastole 120a and the LVIDs 110f in a differentiable manner from others when the M mode measurement 101b is selected as a first layer and the LV Teichholz 101f is selected as a second layer.

Further, in FIG. 6, measurement parameters 'E Vel' and 'A Vel' in a measurement function 'Mitral' 601b are ticked for selection. Here, the 'Mitral' measurement function is a function regarding a blood flow passing through a mitral valve. A blood flow from a left atrial into a left ventricle through the mitral valve shows a bisferious characteristic for a normal or healthy person. In the bisferious characteristic, an earlier pulse is called an E wave and a second one an A wave. A value representing a maximum blood flow velocity measured about the E wave is an E Vel ticked for selection in a measurement function 'Mitral' 401b in FIG. 6. Similarly, a value representing a maximum blood flow velocity measured about the A wave is an A Vel ticked for selection in a measurement function 'Mitral' 401b in FIG. 6. Therefore, for example, this results in displaying measurement parameters of an E Vel and an A Vel in a differentiable manner from others if the M mode measurement 101b is selected as a first layer and the Mitral Valve 101e is selected as a second layer in FIG. 5.

Second Embodiment

Measured value (or data) and/or calculated value (or data) are displayed, for example, in the measured value display area 203 in the measurement screen 200 in a differentiable manner according to a second embodiment of the present invention.

As described above, when desired measurement parameters are selected from a menu such as the measurement parameter selection menu 100 (500) in the touch command screen 13, a measurement screen for measuring the selected measurement parameters is displayed in the monitor 12. Also, in the monitor 12, measurement calipers corresponding to the selected measurement parameters are displayed. When the user places the measurement calipers at one or more measurement positions on the ultrasound image, measured data regarding the measurement positions are displayed in the measured value display area 203. Also, calculated data based on the measured data may be displayed in the measured value display area 203. Further, the user may also draw and determine a desired measurement range with the measurement calipers. For example, an area corresponding to the drawn measurement range is measured and displayed in the measured value display area 203.

An undifferentiated display example of the various measured data and calculated data is shown in FIG. 4. The various measured data and calculated data are displayed in the measured value display area 203 in the measurement screen 200. As shown in FIG. 4, the measurement calipers 201 are displayed on the ultrasound image in the ultrasound image display area 202. In the measured value display area 203 are displayed the measured data and calculated data corresponding to the caliper placed positions or the range drawn by the caliper 201. For example, FIG. 4 shows measured data and calculated data in a use of the LV Teichholz function. As described before, in the LV Teichholz measurement, measurements are implemented on the IVSTd, the LVIDd, the LVPWTd, the IVSTs, the LVIDS, and the LVPWTS. Further, based on these measurements, calculations are implemented on an end-diastolic volume (EDV), an end-systolic volume (ESV), a stroke volume (SV), an ejection fraction (EF), a fractional shortening (FS) and a left ventricle mass at diastole (LV MASSd). The calculated data are displayed with the measured data in the measured value display area 203.

Figure 7:
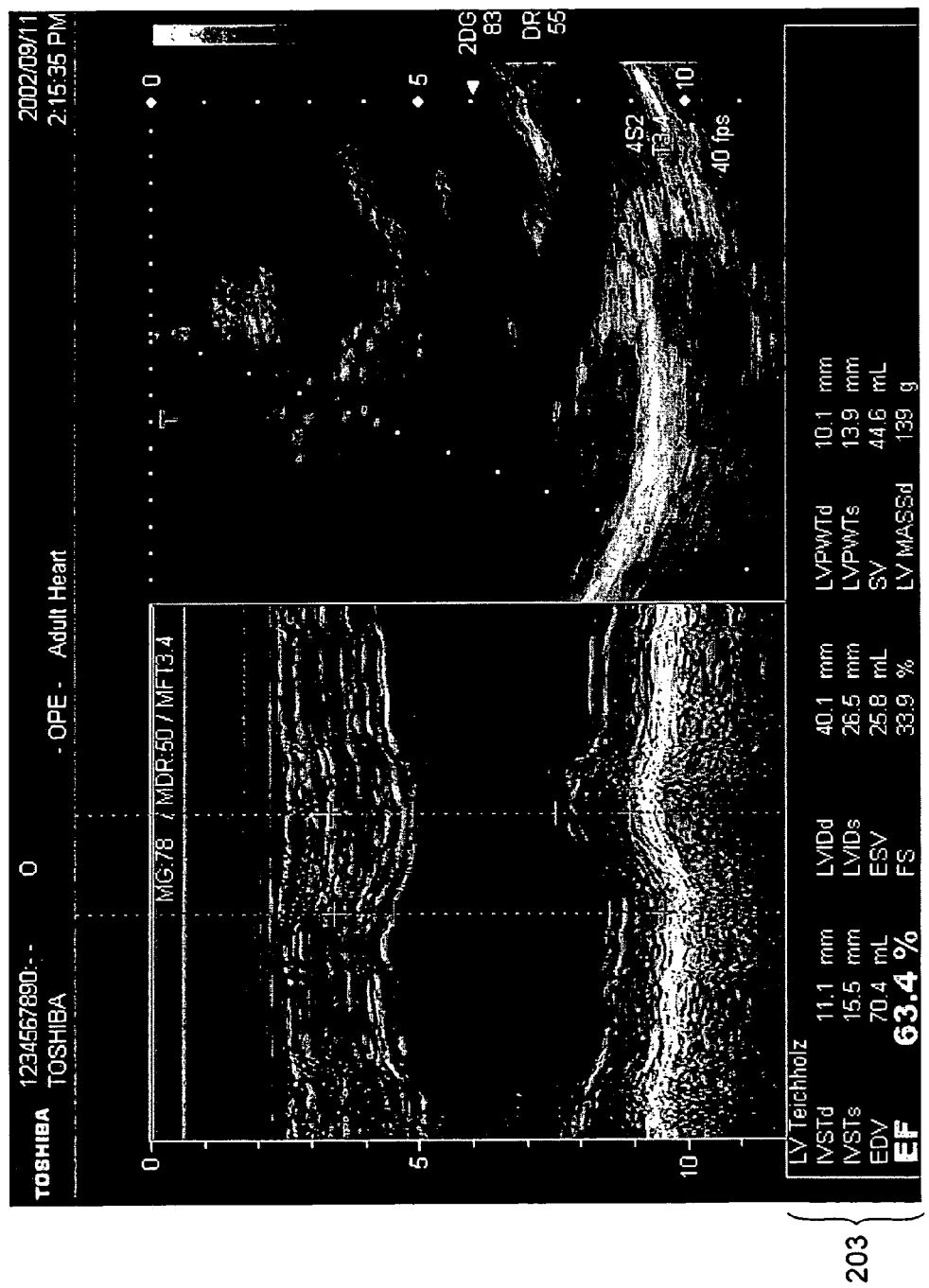
FIG. 7 is an illustration showing a display example according to a second embodiment of the present invention.

FIG. 7 is an illustration showing a display example displayed in the monitor 12 according to the second embodiment of the present invention. One or more measured and/or calculated data can be differentiated from other data. As described before, when the measured data and calculated data are displayed in the measured value display area 203, the control unit 16 reads out parameters to be differentiated and a differentiating manner from the hard disk drive 17. The control unit 16 causes the parameters (here, measured data and/or calculated data) to be displayed in a differentiable manner according to the read-out differentiating manner. For example, as shown in FIG. 7, the calculated data EF regarding the LV Teichholz measurement function is displayed in bold face (in a font different from others) so as to be differentiated. In the measured value display area 203, both the calculated value and the parameter name 'EF' are displayed in the differentiable manner.

For determining which measured data and/or calculated data are differentiated from others in the measured value display area 203, a differentiated display parameter setting menu 800 is used, an example of which is shown in FIG. 8. FIG. 8 is an illustration showing an example of the differentiated display parameter setting menu 800 according to the second embodiment of the present invention. The differentiated display parameter setting menu 800 is displayed in the monitor 12 in response to a user's predetermined operation with the keyboard 14 or the track ball 15. Referring to the differentiated display parameter setting menu 800, the user then selects desired measurement parameters to be differentiated from others. For example, in FIG. 8, a measurement parameter 'EF' in a measurement function 'LV (M) Teichholz' 801 is ticked for selection. This results in displaying the calculated data of the EF in a differentiable manner from others in the measured value display area 203.

Third Embodiment

The measurement calipers 201 are displayed in a measurement screen in a differentiable manner according to a third embodiment of the present invention.

An undifferentiated display example of the measurement calipers 201 is shown in FIG. 4. The measurement calipers 201 are displayed in the ultrasound image display area 202 in the measurement screen 200. For example, FIG. 4 shows the measurement calipers 201 corresponding to the parameter 'EF' in the LV Teichholz measurement function.

Figure 9:
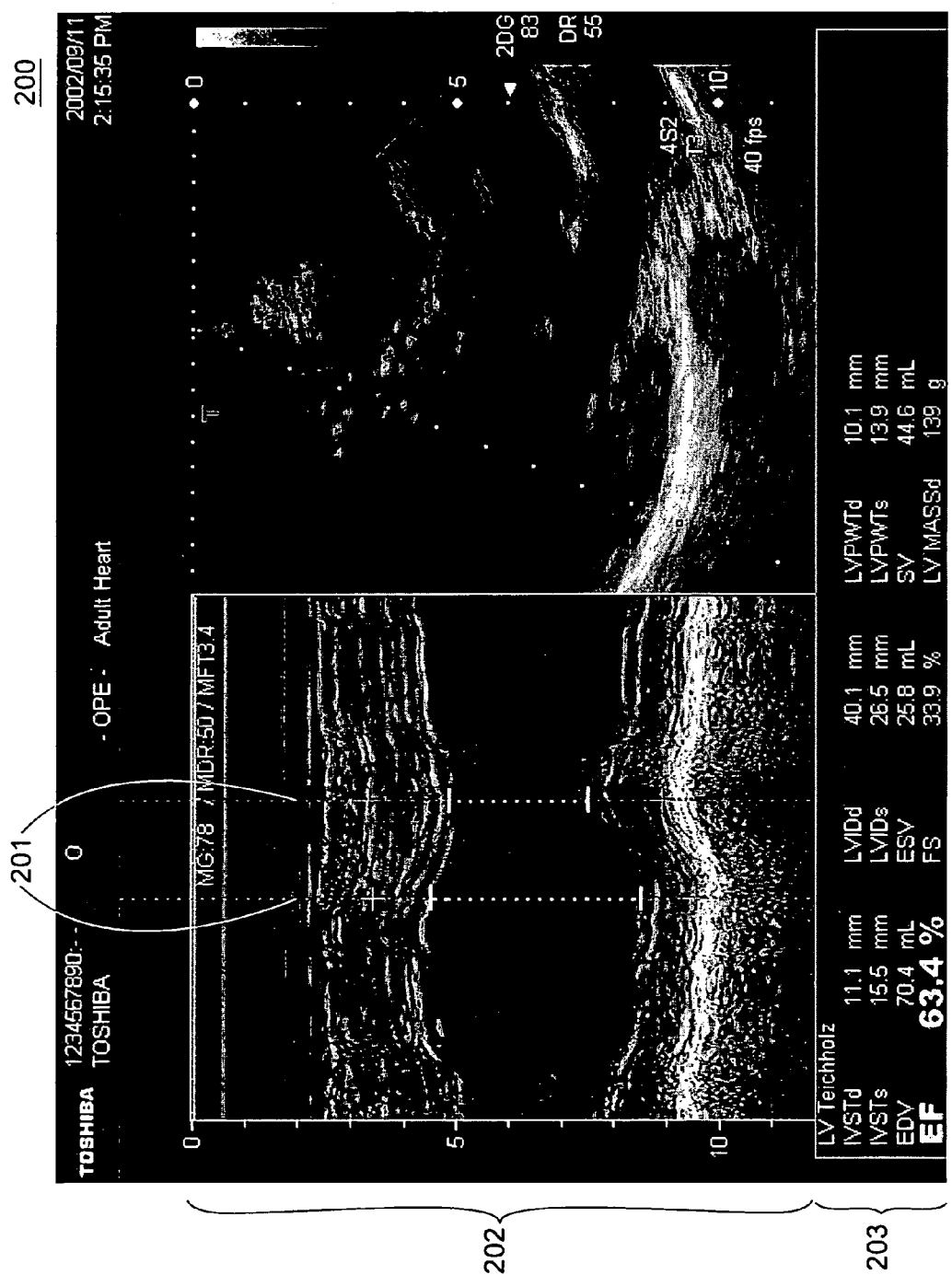
FIG. 9 is an illustration showing a display example according to a third embodiment of the present invention.

FIG. 9 is an illustration showing a display example displayed in the monitor 12 according to the third embodiment of the present invention. One or more measurement calipers can be differentiated from other information displayed in the measurement screen 200. As it will be described later, when the measurement calipers 201 are displayed in the ultrasound image display area 202, the control unit 16 reads out an instruction of whether to differentiate the measurement calipers 201 or not and a differentiating manner from the hard disk drive 17. When the control unit 16 determines that the measurement calipers 201 are instructed to be differentiated, the control unit 16 causes the measurement calipers 201 to be displayed in a differentiable manner according to the read-out differentiating manner. For example, as shown in FIG. 9, the measurement calipers 201 are displayed in bold face (or in a different type of line from calipers that are not displayed in a differential manner) so as to be differentiated.

Figure 10:
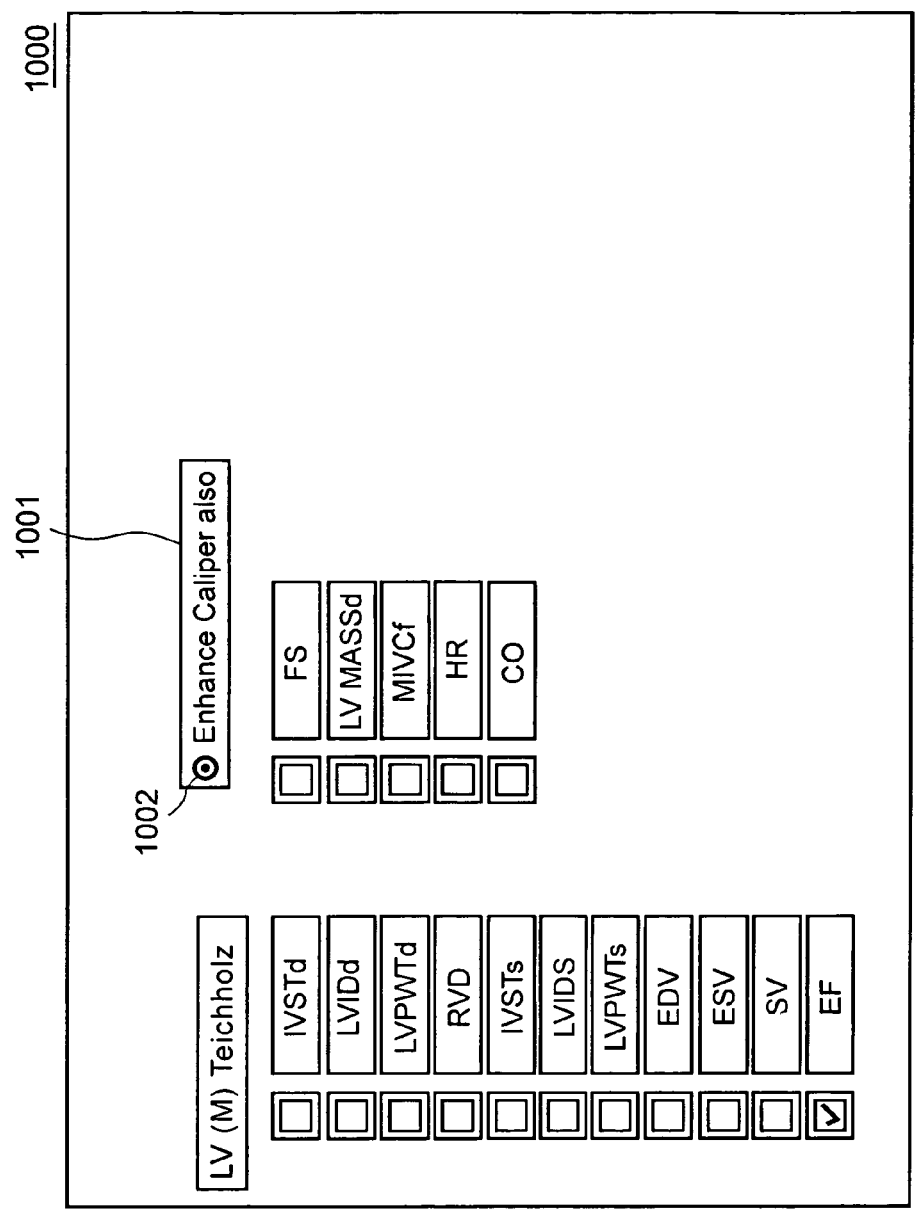
FIG. 10 is an illustration showing an example of a differentiated display parameter setting menu according to the third embodiment of the present invention.

For determining whether measurement calipers 201 are differentiated in the ultrasound image display area 202, a menu such as differentiated display parameter setting menu 1000 is used, which is shown in FIG. 10. FIG. 10 is an illustration showing an example of the differentiated display parameter setting menu 1000 according to the third embodiment of the present invention. The differentiated display parameter setting menu 1000 has a caliper differentiating display setting item 1001 in addition to what is displayed in the differentiated display parameter setting menu 800. The differentiated display parameter setting menu 1000 is displayed in the monitor 12 in response to a user's predetermined operation with the keyboard 14 or the track ball 15. Referring to the differentiated display parameter setting menu 1000, the user then sets a caliper differentiation. For example, in FIG. 10, a checkbox 1002 of the caliper differentiating display setting item 1001 is checked for a differentiating display. The user can also uncheck the checkbox 1002 when the caliper differentiating display is not needed. This results in displaying the measurement calipers 201 in a differentiable manner in the measurement screen 200.

Fourth Embodiment

Measurement parameters and measurement results are displayed in a report in a differentiable manner according to a fourth-embodiment of the present invention. Similarly, calculation parameters and calculation results are also displayed in a report in a differentiable manner according to the fourth embodiment of the present invention.

As described before, when the measurement results and the calculation results are output on paper or transmitted to an external apparatus after the various measurement and calculation with the measurement functions, the user selects an output function. In response to the selection of the output function, a report is displayed in the monitor 12, such as report 1100 as shown in FIG. 11.

An undifferentiated display example of the various measurement results and calculation results is shown in FIG. 11. FIG. 11 is an illustration showing a first example of a report to be output or transmitted according to the fourth embodiment of the present invention. For example, FIG. 11 shows various measurement results and calculation results regarding the LV Teichholz measurement function.

FIG. 12 is an illustration showing a second example of a report to be output or transmitted according to the fourth embodiment of the present invention. A part of the measurement results and the calculation results can be differentiated from others. To be precise, one or more measured data and calculated data as well as their corresponding parameter names are differentiated in a report showing the measurement results and calculation results, for example as in report 1200.

As described before, when the report, such as report 1200, is displayed in the monitor 12, the control unit 16 reads out parameters to be differentiated and a differentiating manner from the hard disk drive 17. The control unit 16 causes the parameters and corresponding measured data and/or calculated data to be displayed in a differentiable manner according to the read-out differentiating manner. For example, as shown in FIG. 12, the calculation result of the parameter EF is displayed in bold face (in a font different from others) in the report 1200 so as to be differentiated. In the report 1200, both the calculated value and the parameter name 'EF' are displayed in the differentiable manner.

For determining which measurement results and/or calculation results are differentiated from others in the report 1200, the differentiated display parameter setting menu 800 is also used, which is shown in FIG. 8. As described in the second embodiment, the differentiated display parameter setting menu, for example differentiated display parameter setting menu 800, is a window for setting measurement parameters to be differentiated in the measured value display area 203 in the measurement screen 200. That is, this differentiated display parameter setting menu 800 is used for both the second and fourth embodiments in common. Under such a common use, the selected parameters are affected for the display in the measurement screen 200 and the report 1200. In this case, it is not necessary to prepare another differentiated display parameter setting menu for the report 1200. Alternatively, another such menu can be prepared.

Further examples will be described below regarding displays of various measurement parameters and calculation parameters in the monitor 12 or the touch command screen 13 of the ultrasound diagnosis apparatus in a differentiable manner.

Fifth embodiment

Another exemplary way will be described regarding a display of measured values (or data) and/or calculated values (or data) in the measured value display area 203 in the measurement screen 200 in a differentiable manner according to a fifth embodiment of the present invention.

Figure 13:
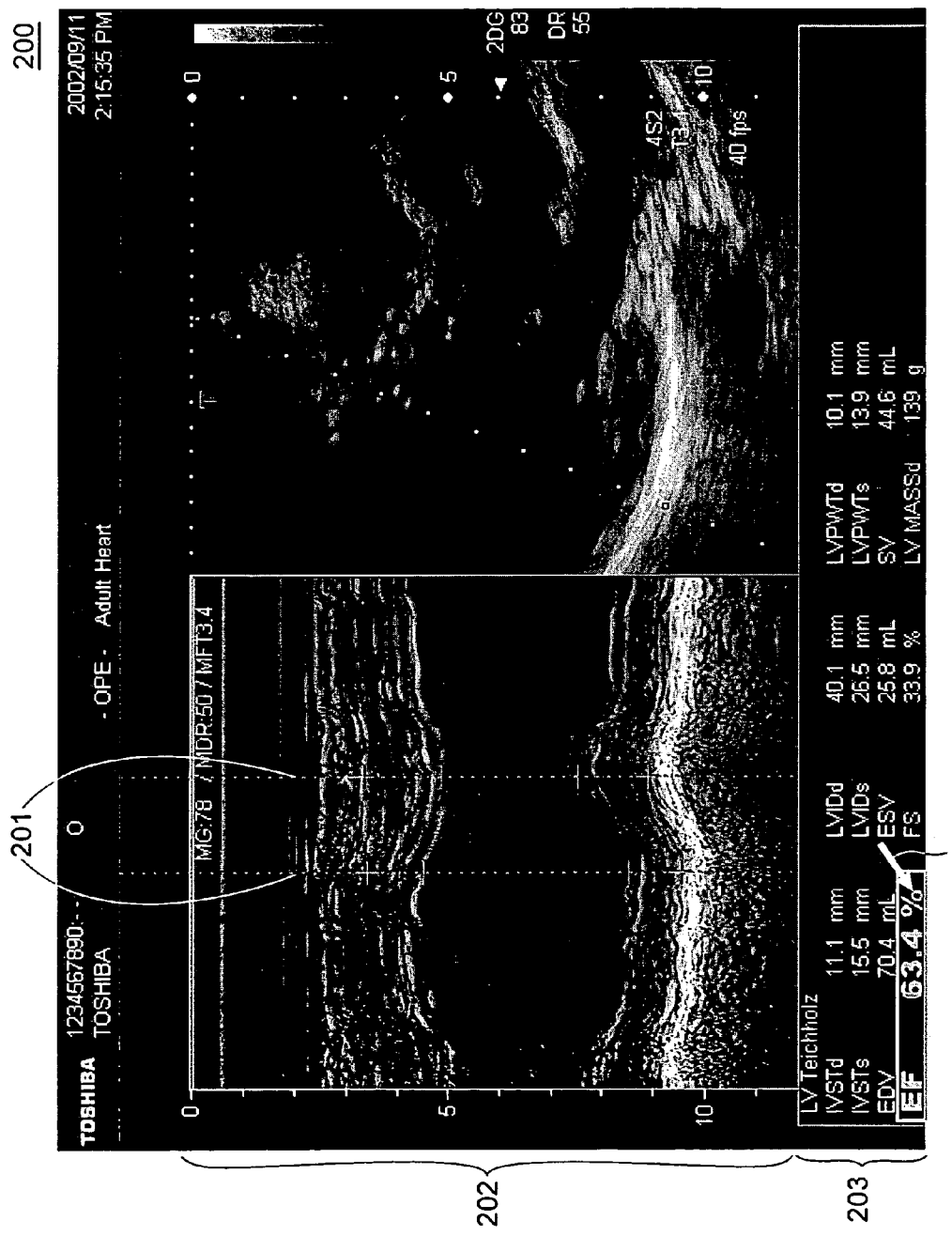
FIG. 13 is an illustration showing a display example according to a fifth embodiment of the present invention.

FIG. 13 is an illustration showing a display example displayed in the monitor 12 according to a fifth embodiment of the present invention. According to the fifth embodiment of the present invention, one measured data or one calculated data can be displayed in the measured value display area 203 in the measurement screen 200 in a differentiable manner without selecting and setting the one measured or calculated data for the differentiating display in advance.

As shown in FIG. 13, various measured data and calculated data are displayed in the measured value display area 203 in accordance with the measurement calipers 201 in the ultrasound image display area 202. The user operates the keyboard 14 or the track ball 15 so as to move a cursor 204 displayed in the measurement screen 200. The user uses the cursor 204 to select one of the measured or calculated data displayed in the measured value display area 203. The data selected (or pointed) by the cursor 204 is displayed in a differentiable manner. Any one of the measured or calculated data, which is pointed by the cursor 204, is displayed in a differentiable manner.

For example, in FIG. 13, the calculated data EF regarding the LV Teichholz measurement function is pointed by the cursor 204 and displayed in bold face (in a font different from others) so as to be differentiated. In the measured value display area 203, both the calculated value and the parameter name 'EF' are displayed in the differentiable manner.

Sixth Embodiment

One or more measurement parameters in a measurement parameter selection menu in a form of a graphic user interface (GUI) are displayed in a differentiable manner according to a sixth embodiment of the present invention.

Figure 14:
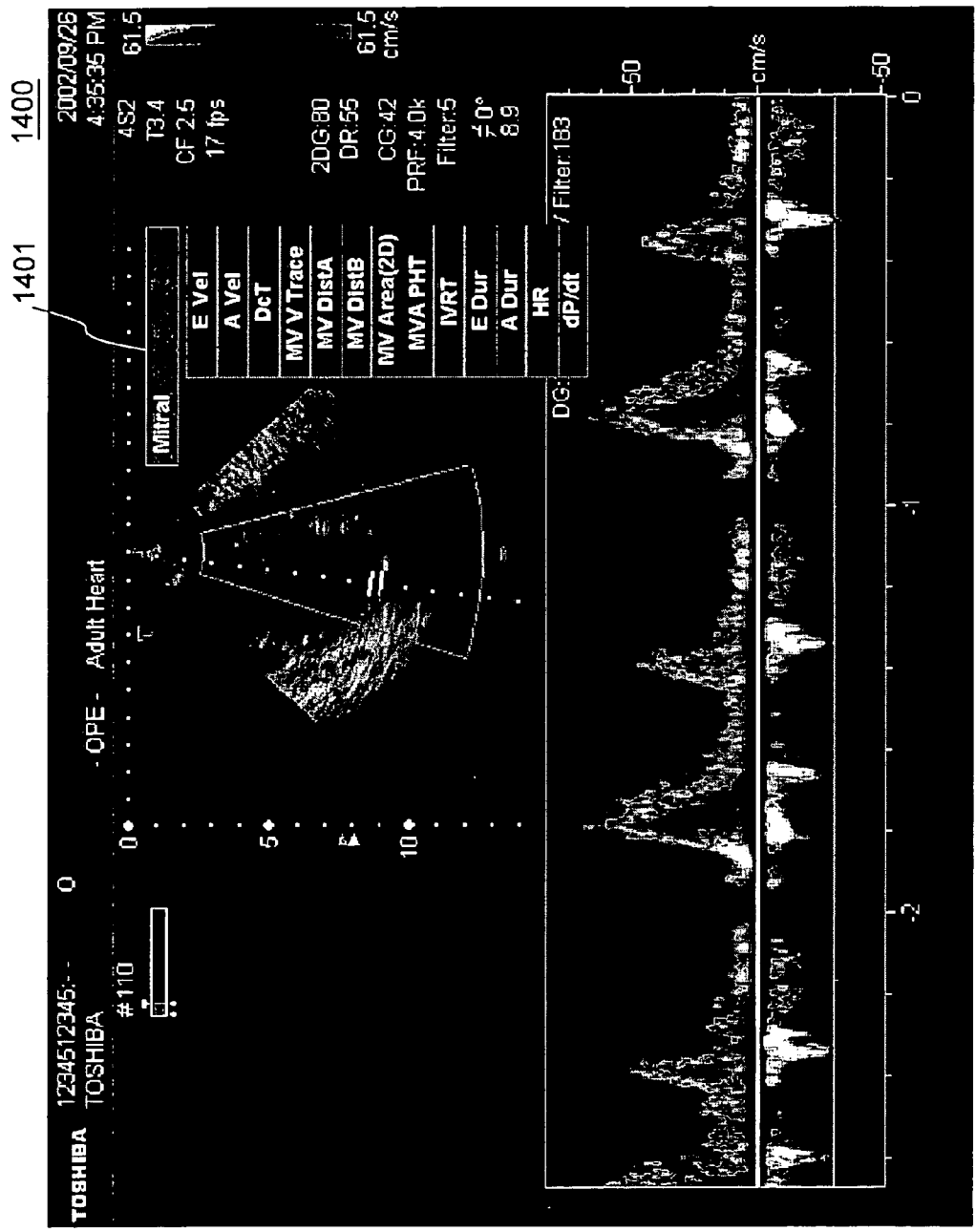
FIG. 14 is an illustration showing a first display example according to a sixth embodiment of the present invention.

FIG. 14 is an illustration showing a first display example displayed in the monitor 12 according to a sixth embodiment of the present invention. FIG. 14 shows a measurement screen 1400 displayed in the monitor 12 when the Doppler mode measurement 101c is selected in the measurement parameter selection menu 100 shown in FIG. 3. As shown in FIG. 14, in response to a user's predetermined operation with the keyboard 14 or the track ball 15, the control unit 16 controls the monitor 12 to display a measurement parameter selection menu 1401 in the measurement screen 1400. The measurement parameter selection menu 1401 is for selecting one or more measurement parameters to be measured and is displayed in a form of GUI. Such a GUI menu display can also be applied to a display in the measurement screen 200. When the user operates the track ball 15 and the like so as to select one or more measurement parameters on the measurement parameter selection menu 1401, measurements are immediately implemented on the selected measurement parameters. Further, the measurement results are displayed in a measured value display area FIG. 14 shows an example of the measurement parameter selection menu 1401 displayed in an undifferentiated manner.

Figure 15:
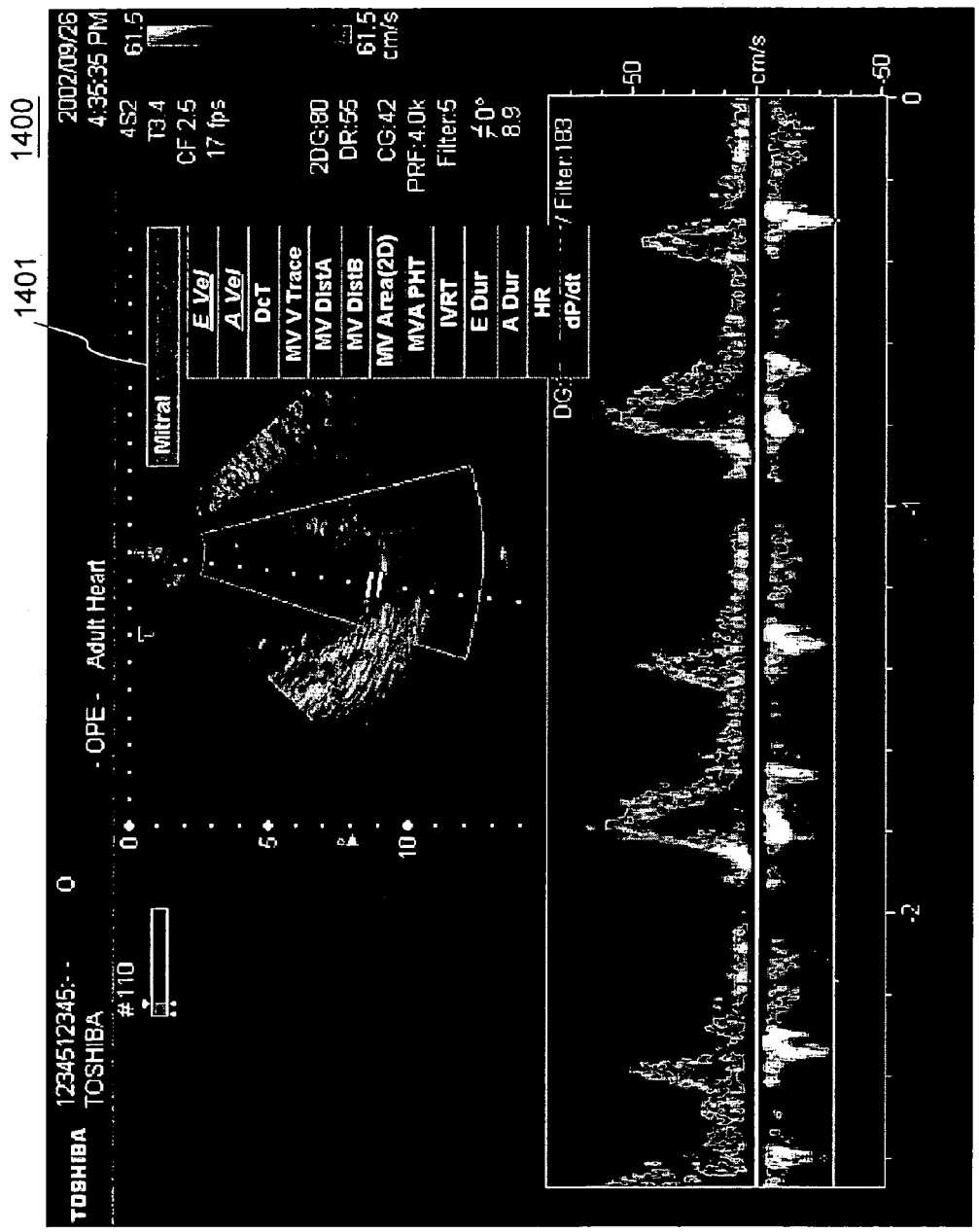
FIG. 15 is an illustration showing a second display example according to the sixth embodiment of the present invention.

FIG. 15 is an illustration showing a second display example displayed in the monitor 12 according to the sixth embodiment of the present invention. One or more measurement parameters can be differentiated from others in the measurement parameter selection menu 1401. When the measurement parameter selection menu 1401 is displayed in the measurement screen 1400, the control unit 16 reads out one or more parameters to be differentiated and a differentiating manner from the hard disk drive 17. The control unit 16 causes the parameters to be displayed in a differentiable manner according to the read-out differentiating manner. For example, as shown in FIG. 15, the measurement parameters 'E Vel' and 'A Vel' regarding a Mitral measurement function are displayed in italic type (in a font different from others) and underlined so as to be differentiated.

For determining which measurement parameters are differentiated from others in the measurement parameter selection menu 1401, a menu such as the differentiated display parameter setting menu 400 is used, which has already been shown in FIG. 6. As described in the first embodiment, the differentiated display parameter setting menu 600 is a window for setting measurement parameters to be differentiated in the measurement election menu 500. That is, this differentiated display parameter setting menu 600 is used for both the first and sixth embodiments in common. Under such a common use, the selected parameters are affected for the display in the measurement selection menu 500 and the measurement parameter selection menu 1401. In this case, it is not necessary to prepare another differentiated display parameter setting menu for the measurement parameter selection menu 1401. Alternatively, another such menu can be prepared.

Seventh Embodiment

A plurality of measured data and calculated data are formed into one group. A plurality of groups are prepared, each of which includes different measurement parameters and calculation parameters from others. Selecting one group leads to a display of a plurality of measurement parameters and calculation parameters included in the selected group in a differentiable manner according to a seventh embodiment of the present invention. Setting a plurality of measurement parameters and calculation parameters as a group will be described with reference to FIG. 16.

Figure 16:
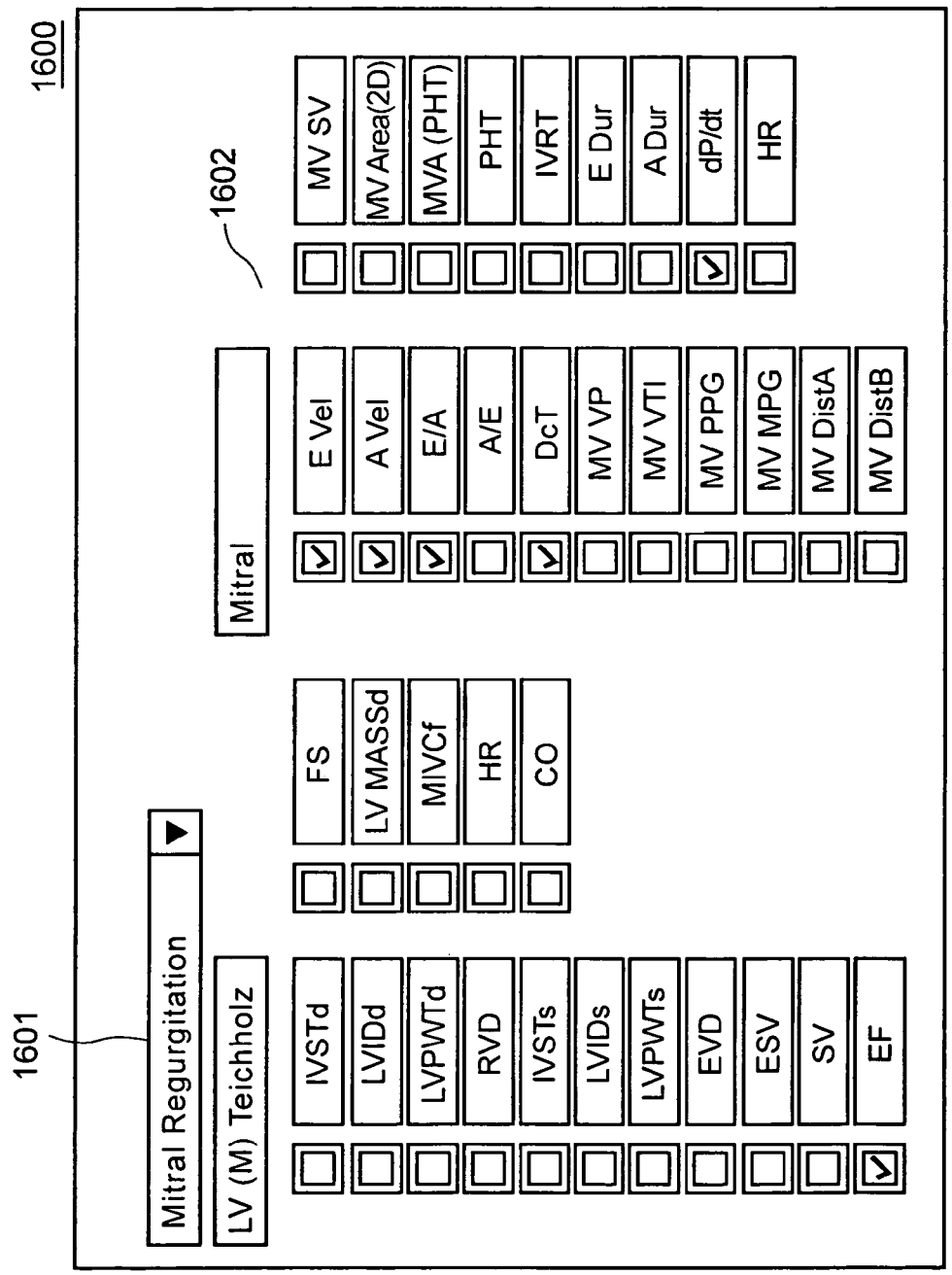
FIG. 16 is an illustration showing an example of a differentiated display parameter setting menu according to a seventh embodiment of the present invention.

FIG. 16 is an illustration showing an example of a differentiated display parameter setting menu according to the seventh embodiment of the present invention. The grouped measurement parameters and calculation parameters are displayed in a measured value display area in a measurement screen or displayed in a report in a differentiable manner from others.

A differentiated display parameter setting menu 1600 shown in FIG. 16 has a differentiated display group setting menu 1601 and a differentiated display parameter setting menu 1602 corresponding to a group set in the differentiated display group setting menu 1601, in addition to what is displayed in the differentiated display parameter setting menu 800. The differentiated display parameter setting menu 1600 is displayed in the monitor 12 in response to a user's predetermined operation with the keyboard 14 or the track ball 15. Referring to the differentiated display group setting menu 1601, the user then selects a desired group to be differentiated. For example, in FIG. 16, a 'Mitral Regurgitation' group is selected in the differentiated display group setting menu 1601. In response to the selection of the 'Mitral Regurgitation' group, a plurality of measurement parameters and calculation parameters both of which corresponding to the selected group 'Mitral Regurgitation' are displayed in the differentiated display parameter setting menu 1600.

In the differentiated display parameter setting menu 1600, a plurality of predetermined measurement parameters and calculation parameters are automatically ticked as a default selection. When the user agrees to the default selection, the user operates the keyboard 14 or the track ball 15 so as to input an agreement instruction. If the user does not agree to the default selection, the user unchecks one or more undesirable parameters. In addition or alternatively, the user checks off one or more desirable parameters which are not included in the default selection. The user's selection may be reflected for the next selection as a default. As a result, the user only needs to select a desired group for the display. In FIG. 16, for example, the default section for the selected group 'Mitral Regurgitation' includes the parameter EF in the measurement function 'LV (M) Teichholz', parameters E Vel, A Vel, E/A, DcT, and dP/dt in a measurement function 'Mitral'. Accordingly, the parameters included in the selected group are displayed in a window, such as, for example, the measurement screen 200 in FIG. 4, in a differentiable manner from other parameters.

The group selection and the differentiated parameter display according to the group selection may also be applied to a report, such as, for example, the repor 1200 shown in FIG. 12. In this case, it is not necessary to implement the parameter selection and setting to be displayed in the report 1200 in a differentiable manner de novo. Alternatively, an original differentiated display parameter setting menu similar to the differentiated display parameter setting menu 1600 may be prepared for a group setting. Accordingly, one or more measurement parameters and calculation parameters corresponding to parameters included in a selected group are displayed in a differentiable manner in the report 1200.

As described above, when various measurements and calculations for an ultrasound image diagnosis are implemented in the ultrasound diagnosis apparatus according to the embodiments of the present invention, the user can select and set specific or desired parameters and data, in advance or at a necessary moment, for a differentiating display among a number of parameters and data to be displayed. This results in improvement of visibility in the monitor 12.

The differentiable manners in the display of parameters and data in the ultrasound diagnosis apparatus according to the embodiments of the present invention are not limited to the already described manners such as a character style, a character font, a line type, and an underline. Other differentiable manners may also be applied to the display of parameters and data. For example, a display in a different color, a different size, a different shape, a blinking, and/or any combination of these may be advantageous. Further, one or more words such as 'Note', for example, or symbols may be added to the parameters or data to be differentiated from others. Information other than the specific parameters and data may alternatively be tinted so as to highlight the specific parameters and data.

Still further, a differentiating level or degree may be given in some steps. The level or degree may be determined based on how important each parameter or data is. The steps may be differentiated in color, symbol, or with a word such as 'Very Important', 'Important', or 'Slightly Important', according to the importance.

Eighth Embodiment

Annotation items including annotation characters and annotation symbols are displayed in an annotation selection menu displayed, for example, in the touch command screen 13 in a differentiable manner according to an eighth embodiment of the present invention.

Referring to the ultrasound images displayed in the monitor 12, the user may add one or more annotations to the ultrasound images as a comment, a memorandum, a note, a caution, and/or the like so as to easily recognize and remember later, or let other users recognize what should be noted of the images.

Figure 17:
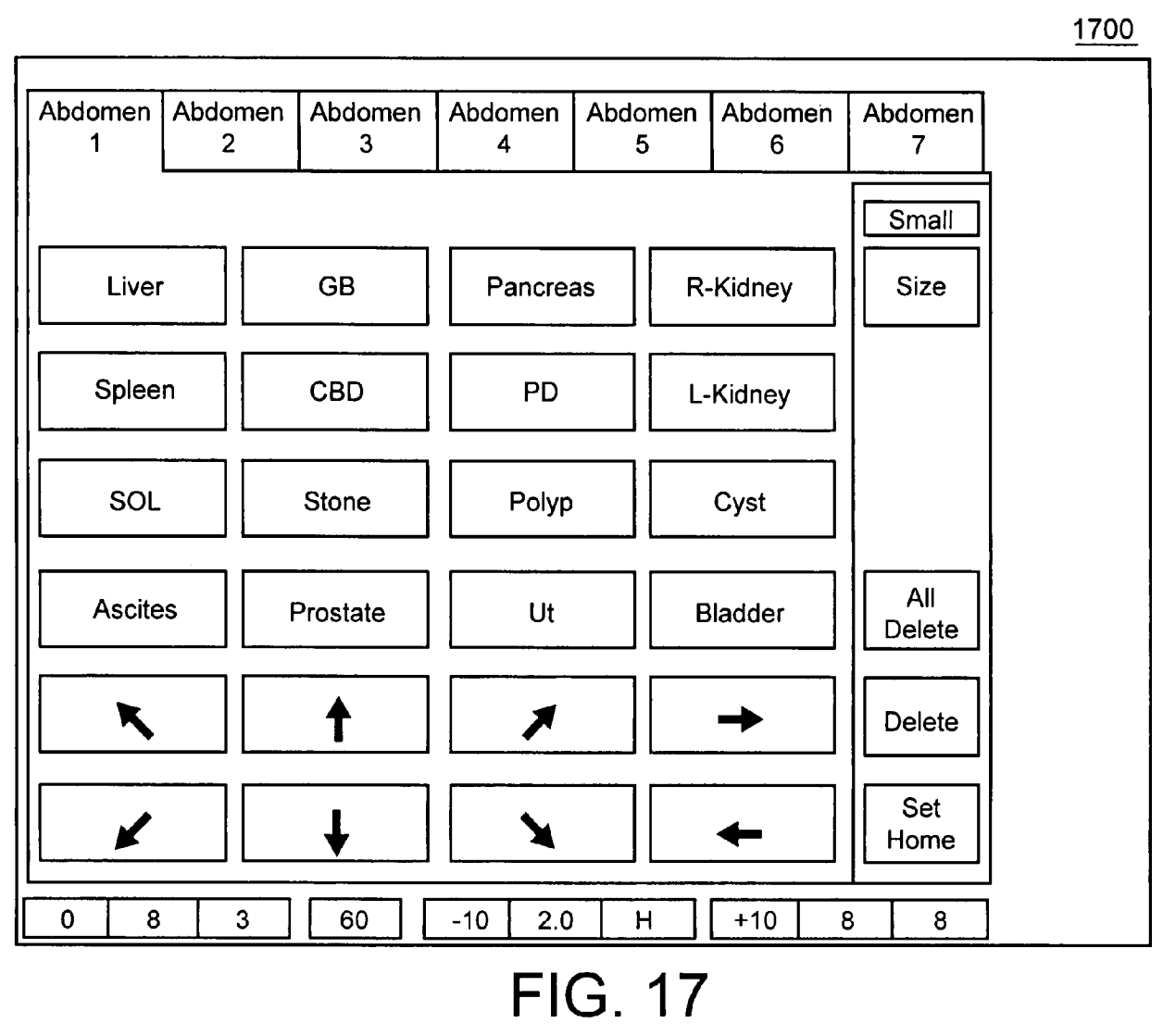

FIG. 17 is an illustration showing a first exemplary display of the touch command screen 13 according to an eighth embodiment of the present invention. In the touch command screen 13, an annotation selection menu 1700 is displayed, having a plurality of annotation items as shown in FIG. 17. The annotation selection menu 1700 shows seven tab sheets prepared for abdomen. Such annotation selection menu 1700 may be prepared for various parts of a human body or any other necessary classifications, respectively.

When the user annotates the ultrasound images displayed in the monitor 12, the annotation selection menu 1700 is displayed in the touch command screen 13 in response to a user's predetermined operation. The user selects one or more annotation items in the annotation selection menu 1700 and applies each of the selected annotation items to each appropriate position in the displayed ultrasound images. For example, the selection and application may be accomplished by touching a desired annotation item in the annotation selection menu 1700 for the selection and placing a cursor and clicking at a desired position of the displayed ultrasound images. Accordingly, an annotation corresponding to the selected annotation is displayed on the ultrasound images.

If, however, there are a number of annotation items in each of a number of tab sheets for each of a number of, for example, body parts, it is not easy for the user to remember where a desired annotation item is present. This troubles the user for finding the desired annotation item immediately, and may lead to frustrating the user, which may affect user's image interpretation.

Therefore, similar to the embodiments described above, one or more annotation items can be selected in advance for a differentiating display in a menu, such as the annotation selection menu 1700.

FIG. 18 is an illustration showing a second exemplary display of the touch command screen 13 according to the eighth embodiment of the present invention. As shown in FIG. 18, an annotation selection menu 1800 has some annotation items differentiated from others. Such a display in a differentiable manner may be accomplished by using a differentiated display annotation setting menu which may be similar to one of those shown in FIGS. 6, 8, 10, and 16. In FIG. 18, for example, annotation items 'Liver', 'Spleen', 'Pancreas', 'R-Kidney', and 'L-Kidney' are displayed in bold face and underlined so as to be differentiated from others. As a result of such a display, the user can easily recognize desired or often-used annotation items. This display may contribute to improvement of an image interpretation efficiency by the user.

Ninth Embodiment

Annotations including annotation characters and annotation symbols are displayed on the ultrasound images displayed in the monitor 12 in a differentiable manner according to a ninth embodiment of the present invention.

Figure 19:
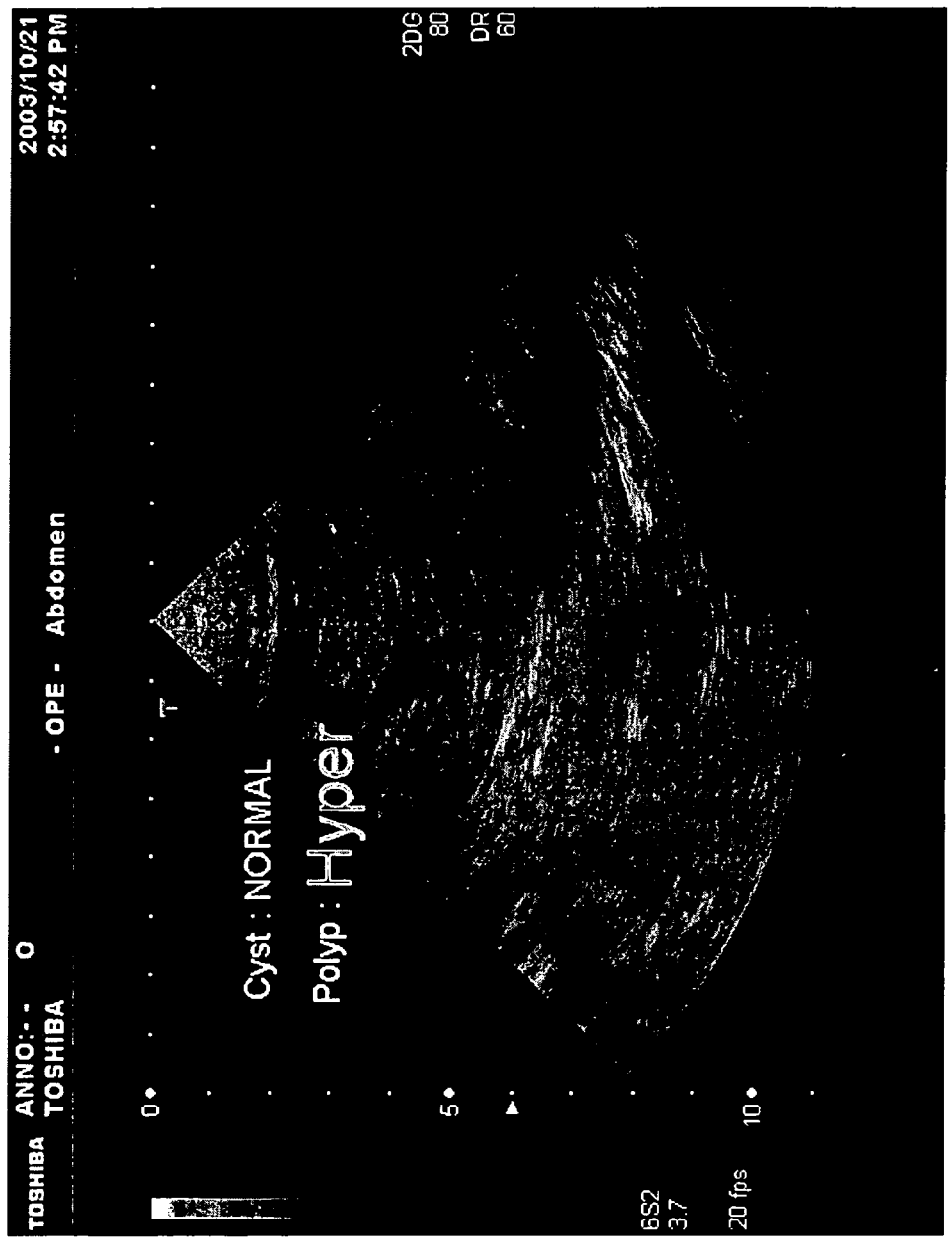
FIG. 19 is an illustration showing a display example according to a ninth embodiment of the present invention.

FIG. 19 is an illustration showing a display example according to a ninth embodiment of the present invention. In FIG. 19, a specific annotation 'Hyper' is displayed in a differentiable manner from other annotations displayed on the ultrasound image.

One or more annotations to be displayed in a differentiable manner are basically not related to those displayed in the annotation selection menu 1800 in FIG. 18. Annotations to be displayed on the ultrasound images in a differentiable manner can be independent from annotation items displayed in the annotation selection menu 1800 in a differentiable manner. Therefore, for selecting and setting annotations to be displayed on the ultrasound images in a differentiable manner, another differentiated display annotation setting menu is prepared, which may be similar to one of those shown in FIGS. 6, 8, 10, and 16. Alternatively, the annotations to be displayed on the ultrasound images in a differentiable manner may be identical to the annotation items displayed in the annotation selection menu 1800 in a differentiable manner. In this case, it is not necessary to prepare another differentiated display annotation setting menu for the differentiating display on the ultrasound images.

Tenth Embodiment

Body symbols (or marks) each of which represent a position and direction of the ultrasonic probe 1 on the human's body, are displayed in the touch command screen 13 in a differentiable manner according to a tenth embodiment of the present invention.

The user may select one of the body symbols, which is appropriate for showing an actual position and direction of the ultrasonic probe 1 in an ultrasound examination. The selected body symbol is displayed on the ultrasound image. The displayed symbol helps the user to recognize later again or to let other user to recognize the examined position and direction.

Figure 20:
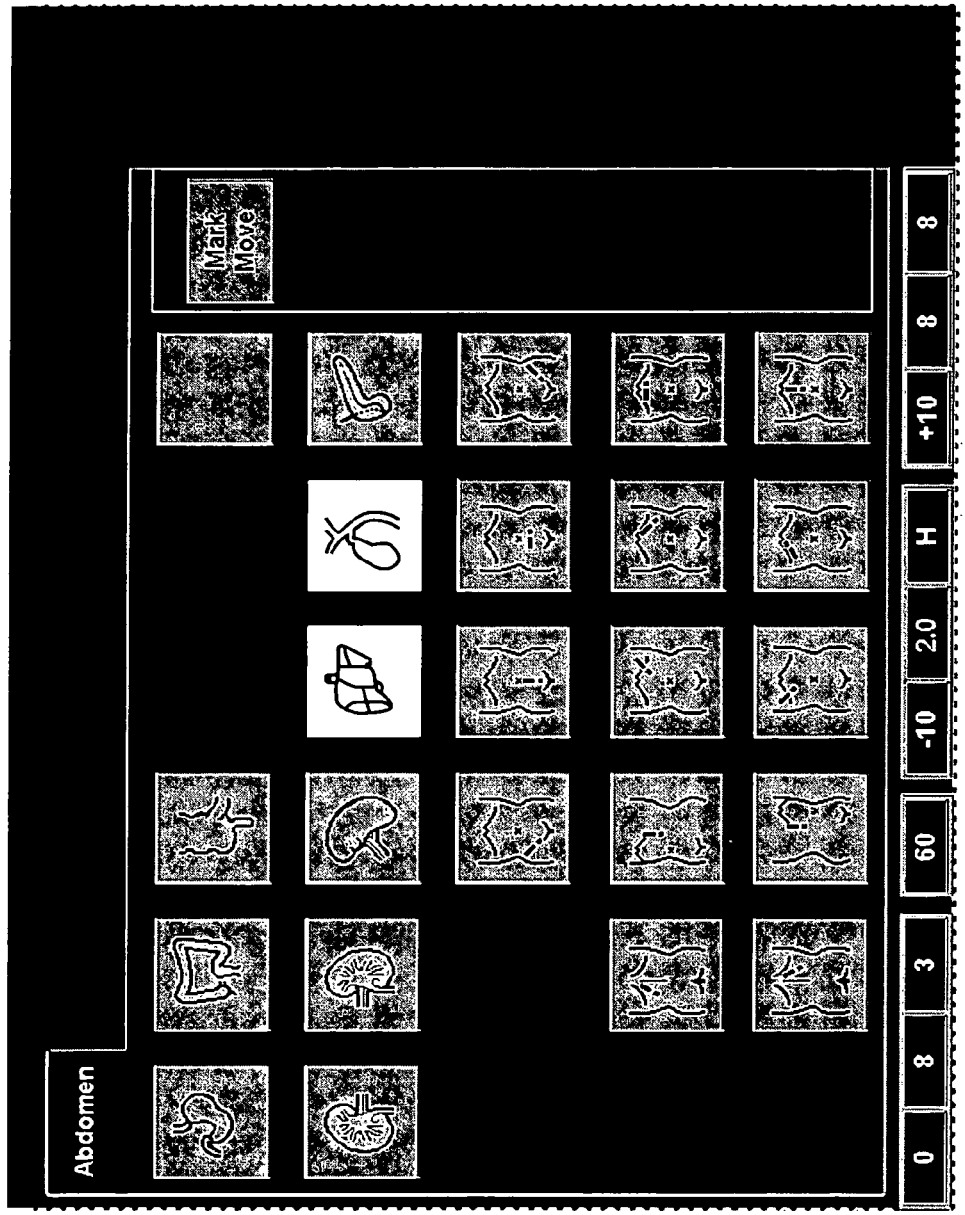
FIG. 20 is an illustration showing an exemplary display of the touch command screen according to a tenth embodiment of the present invention.

FIG. 20 is an illustration showing an exemplary display of the touch command screen 13 according to a tenth embodiment of the present invention. As shown in FIG. 20, one or more body symbols are displayed in a differentiable manner in a body symbol selection menu 2000 displayed in the touch command screen 13. Body symbols which are often used may be displayed in a differentiable manner so that it takes less time on average for the user to find a desired body symbol. For selecting and setting body symbols to be displayed in a differentiable manner, a differentiated display body symbol setting menu is used, which may be similar to one of those shown in FIGS. 6, 8, 10, and 16.

The menu, such as body symbol selection menu 2000 is displayed in the touch command screen 13 in response to a user's predetermined operation. When the user selects one of the body symbols from the body symbol selection menu 2000, the selected body symbol is displayed on the ultra sound image. The display position on the ultrasound image is predetermined. Alternatively, the display position may be determined by the user. For example, the selection and display may be accomplished by touching a desired body symbol in the body symbol selection menu 2000 for the selection so that the touched body symbol is automatically displayed at the predetermined position on the ultrasound image. Alternatively, the touched body symbol may be displayed at a position on the ultrasound image clicked on by the user.

Whether the selected body symbol is one displayed in the body symbol selection menu 2000 in a differentiable manner or not, the selected body symbol is displayed on the ultrasound image in an undifferentiated manner. Such a selected body symbol displayed in the body symbol selection manner 2000 in a differentiable manner may alternatively be displayed on the ultrasound image in a differentiable manner.

Eleventh Embodiment

The above described measurement processing and calculation processing are not necessarily implemented in the ultrasound diagnosis apparatus. Any of the above described embodiments of the present invention can also be applied to medical information processing apparatus. Some examples in the medical information processing apparatus will be described below. Although the examples will be described as a case of ultrasound images, any medical image or information, if applicable, can be applied to the following description.

Figure 21:
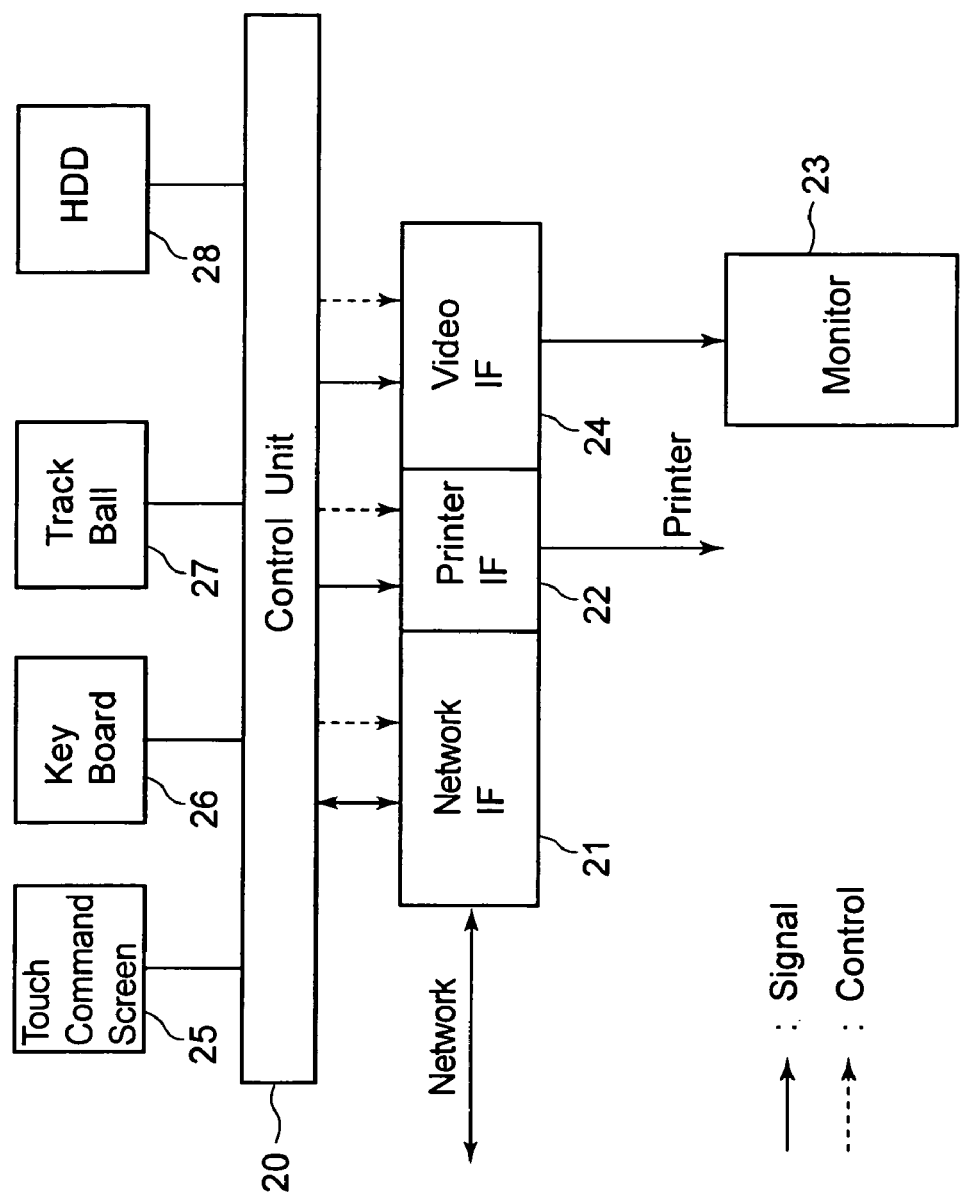
FIG. 21 is a block diagram showing an exemplary configuration of a medical information processing apparatus according to an eleventh embodiment of the present invention.

FIG. 21 is a block diagram showing an exemplary configuration of a medical information processing apparatus according to an eleventh embodiment of the present invention. In FIG. 21, the medical information processing apparatus includes a control unit 20 that controls the medical information processing apparatus, a network interface 21 that connects the control unit 20 to an external ultrasound diagnosis apparatus, a printer interface 22 which connects the control unit 20 to an external printer, a monitor 23 that displays images and data, and a video interface 24 that connects the control unit 20 to the monitor 23. The medical information processing apparatus further includes a touch command screen 25 that is used for a display and an input of designation and setting, a keyboard 26, a track ball 27, both of which are used for an input of designation and setting, and a hard disk drive 28 that stores data and ultrasound image data received from the external ultrasound diagnosis apparatus through the network interface 21.

The medical information processing apparatus receives ultrasound image data from the external ultrasound diagnosis apparatus through the network interface 21. The ultrasound image data are signals mapped to positions corresponding to transmission and reception of the ultrasound beam by scan converters in the external ultrasound diagnosis apparatus. The received ultrasound image data are output to the video interface 24 from the control unit 20. Finally, ultrasound images are displayed based on the received ultrasound image data in the monitor 23.

When the ultrasound images are displayed in the monitor 23, the user operates the touch command screen 25, the keyboard 26, and/or the trackball 27 for various measurements on an objective part of the displayed ultrasound images. The various measurements include a measurement of a distance and a measurement of a blood flow speed. In response, the control unit 20 implements various measurements in accordance with the user's operation. The control unit 20 causes the measurement results and calculation results calculated based 6n the measurement results to be displayed in the monitor 23. The control unit 20 implements displaying controls over the monitor 23 and the touch command screen 25.

When the user operates the touch command screen 25, the keyboard 26, and/or the track ball 27 to differentiate specific one or more of various measurement parameters and calculation parameters displayed in the touch command screen 25 (or the monitor 23), the control unit 20 controls in response to the user's operation and causes the specific one or more measurement parameters and/or calculation parameters to be displayed in a differentiable manner from other measurement parameters and calculation parameters. Here, the 'parameters' indicate parameter items (or names) and/or values, as necessary. Information regarding possible differentiable manner of measurement parameters and/or calculation parameters is stored in the hard disk drive 28. Accordingly, the control unit 20 implements differentiating processing on specific (or designated) parameters in accordance with the differentiable manner stored in the hard disk drive 28.

Similar to the ultrasound diagnosis apparatus described in the above described embodiments, the medical information processing apparatus incorporates an application program for measurements. The application program realizes, for example, a measurement of a structural size, such as a distance, an area, and a volume of various tissues based on B mode images. The application program also realizes, for example, a measurement of temporal variation based on M mode images. As shown in FIG. 2, the application program installed in the medical information processing apparatus includes a measurement function, output function, and differentiating designation function.

When the user performs an ultrasound diagnosis, the user may first use a measurement function so as to measure and calculate various parameters. Next, the user may use an output function to output a result of the measurement and calculation on paper or to an external apparatus. In addition, however, when the user prefers to see specific one or more parameters in a differentiable manner from other parameters in the monitor 23 and/or the touch command screen 25 during a use of the above functions, the user can use a parameter differentiating designation function in advance of or during the use of the measurement or the output function so as to designate desired parameters to be displayed in a differentiable manner.

Selecting one of the functions including the above three functions is, for example, accomplished by the user's using the keyboard 26 or the track ball 27 for a GUI menu displayed in the monitor 23 . Alternatively, for example, the user may touch and select a desired function item in a function selecting view displayed in the touch command screen 25.

In more detail, when the user selects the measurement function, the measurement parameter selection menu 100 is displayed in the touch command screen 25 as shown in FIG. 3. When measurement parameters are displayed in the measurement parameter selection menu 100, the control unit 20 reads out parameters to be differentiated and a differentiating manner from the hard disk drive 28. The control unit 20 causes the measurement parameters to be displayed in a differentiable manner according to the read-out differentiating manner (See FIG. 5, for example). The user selects desired measurement parameters by touching one or more parameters in the measurement parameter selection menu 100. Alternatively, the user operates the keyboard 26 or the track ball 27 so that a GUI menu is displayed in the monitor 23. The user can select the desired measurement parameters in the displayed GUI menu. Accordingly, a measurement screen corresponding to the selected measurement parameters is displayed in the monitor 23 (See FIG. 4, for example). In the measurement screen, measurement calipers are displayed in an ultrasound image display area. Also, measured data and calculated data based on the measurement calipers are displayed in a measured value display area. For this display, the control unit 20 reads out parameters to be differentiated and a differentiating manner from the hard disk drive 28. The control unit 20 causes the parameters to be displayed in a differentiable manner according to the read-out differentiating manner (See FIG. 7, for example).

After the measurements and the calculations by the measurement function, when the user selects the output function for outputting the measurement result and the calculation results on a paper or to an external apparatus, a report showing a list of various measurement results and calculation results is displayed in the monitor 23 (See FIG. 11, for example). When the measurement results and the calculation results are displayed in the report, the control unit 20 reads out parameters to be differentiated and a differentiating manner from the hard disk drive 28. The control unit 20 causes the parameters to be displayed in a differentiable manner according to the read-out differentiating manner (See FIG. 12, for example). In this output function, a displayed content of the report can be output to a video cassette recorder, a DVD recorder, or the like through the video interface 24 in response to a user's predetermined operation with the keyboard 26 or the track ball 27. Similarly, the displayed content of the report can also be output to the external printer through the printer interface 22. Further, when there is an external apparatus such as an image management server communicably connected to the medical information processing apparatus, the displayed content of the report can also be output to the external apparatus through the network interface 21. In case that the external apparatus is, for example, a DICOM (Digital Imaging and Communication for Medicine) server, the control unit 20 adds a flag for the differentiating display to the measured data and calculated data. When the measured data and calculated data with the flag are transmitted to the DICOM server, the differentiating display is realized in the DICOM server.

While the user is using the measurement function or the output function, the user can select the parameter differentiating designation function in advance of or during the use of the functions so as to display one or more of the various measurement parameters, the calculation parameters, the measurement results, and the calculation results in the touch command screen 25 in a differentiable manner. In this case, for example, a differentiated display parameter setting menu is displayed in the monitor 23 (See FIG. 8, for example). In FIG. 8, various measurement parameters in a measurement function 'LV (M) Teichholz' are displayed. When the various measurement parameters are displayed in the differentiated display parameter setting menu, the control unit 20 reads out parameters to be differentiated and a differentiating manner from the hard disk drive 28. The control unit 20 controls the monitor 23 to display the read-out parameters as currently stored parameters for the differentiating display. The user operates the keyboard 26 or the trackball 27 in the differentiated display parameter setting menu so as to select desired measurement parameters to be differentiated. For example, the differentiated display parameter setting menu is prepared for setting parameters to be displayed in a differentiable manner, among parameters to be displayed in the measured value display area in the measurement screen displayed in the monitor 23 (See FIGS. 4 and 8, for example). In addition, another differentiated display parameter setting menu is prepared for setting parameters to be displayed in a differentiable manner, among various measurement parameters in the measurement parameter selection menu 100 displayed in the touch command screen 25 (See FIGS. 3, 5 and 6. Further, still another differentiated display parameter setting menu is prepared for setting measurement results and calculation results to be displayed in a differentiable manner, among various measurement results and calculation results in the report to be displayed in the monitor 23 (See FIGS. 11 and 12, for example). What are selected or set in the above differentiated display parameter setting menu are stored in the hard disk drive 28, and are read out by the control unit 20.

Summary of displays of various measurement parameters, calculation parameters, and the like in a differentiable manner has been described above, with respect to the medical information processing apparatus according to the eleventh embodiment of the present invention. Details, however, that is, for example, various types of differentiating displays of various measurement parameters, calculation parameters, measured data, calculated data, and calipers are similar to those described in the first to tenth embodiments of the present invention and therefore omitted herein.

As described above, when various measurements and calculations are implemented for an ultrasound image diagnosis in the medical information processing apparatus according to the eleventh embodiment of the present invention, the user can select and set specific or desired parameters and data, in advance or at a necessary moment, for a differentiating display among a number of parameters and data to be displayed. This results in improvement of visibility in the monitor 23.

In the embodiments of the present invention, the ultrasound diagnosis apparatus or the medical information processing apparatus may have a random access memory (RAM), which can receive and store computer programs and applications as computer readable instructions in a temporary and/or non-volatile state. The ultrasound d diagnosis apparatus or the medical information processing apparatus may further have a hard disk drive as part of the units for reading from and writing to a hard disk, a magnetic disk drive for reading from and writing to a magnetic disk, and/or an optical disk drive for reading from and writing to an optical disk (such as a CD, CDR, CD-RW, DVD, or other optical device). Those skilled in the art will appreciate that one or more of such memory, drives, and their respective media are examples of a computer program product for storing computer readable instructions, which when executed, may implement an embodiment of the present invention.

Accordingly, an ultrasound diagnosis apparatus or a medical information processing apparatus connected to an ultrasound diagnosis apparatus which does not incorporate features of embodiments of the present invention can benefit the features as long as the ultrasound diagnosis apparatus or the medical information processing apparatus is equipped with a feature of displaying ultrasound images and inputting information as well as a feature of reading and performing a computer readable program.

In the embodiments of the present invention, parameters, data, and items to be displayed in a differential manner may be set and stored for every user according to the user's preference.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. A medical imaging apparatus for generating medical information regarding a plurality of measurement parameters, comprising:
   a plurality of input units including a measurement parameters selection menu screen, a keyboard, and a track ball operable by a user and configured to selectively input an instruction for selecting measurement parameters among the plurality of measurement parameters to be displayed in an emphasized manner on a processed medical image;
   a plurality of scan converters configured to execute measuring processes and to output mapped signals based on the instruction associated with the selected measurement parameters;
   a plurality of interfaces including a video interface configured to output the mapped signals to a monitor, a printer interface configured to output the mapped signals to a printer, and a network interface configured to output the mapped signals to a remote medical imaging apparatus through a network;
   a processor configured to generate a graphical user interface that includes a plurality of body symbols that depict a position and direction of a probe of the medical imaging apparatus on a human body, wherein the graphical user interface allows a user to select one of the body symbols, and at least one of the body symbols is displayed in an emphasized manner;
   a first display configured to display the processed medical image associated with the selected measurement parameters, wherein the one of the body symbols selected by the user is displayed on the processed medical image;
   a first setting unit configured to set a first part of display information among medical information of the selected measurement parameters to be displayed in the emphasized manner from non-selected measurement parameters; and
   a display controller configured to automatically display the first part of the display information of the selected measurement parameters in the emphasized manner on the first display of the processed medical image, which is a different display than the measurement parameters selection menu, and on a second display of another image, subsequent to the first display of the processed medical image, without reselecting measurement parameters to be emphasized such that the selected measurement parameter is always displayed in the emphasized manner whenever the display controller causes the processed medical image or the another image to be displayed on or printed by either one or more of the monitor, the printer, and the remote medical imaging apparatus which are selected by the plurality of interfaces.

2. The apparatus according to claim 1, further comprising a second input unit configured to input a second instruction for selecting a second part of the display information displayed in the first display, and a second display configured to display the second part in accordance with the second instruction.

3. The apparatus according to claim 1, wherein the first display is further configured to display a menu list of the display information, and
   the display controller controls the first part of the display information selected in the menu list of the display information.

4. The apparatus according to claim 3, wherein the first display is further configured to display the menu list with a medical image when the medical image is included in the medical information.

5. The apparatus according to claim 1, wherein the medical information includes a medical image.

6. The apparatus according to claim 5, further comprising a second processor configured to implement a measurement on the medical image, and wherein the first part of the display information includes a measurement parameter name in the measurement.

7. The apparatus according to claim 5, further comprising a second processor configured to implement a measurement on the medical image, and wherein the first part of the display information includes a measurement parameter value resulting from the measurement.

8. The apparatus according to claim 5, further comprising a second processor configured to implement a measurement on the medical image, and wherein the first part of the display information includes a calculation parameter name of a calculation based on a measurement parameter value resulting from the measurement.

9. The apparatus according to claim 5, further comprising a second processor configured to implement a measurement on the medical image, and wherein the first part of the display information includes a calculation parameter value calculated based on a measurement parameter value resulting from the measurement.

10. The apparatus according to claim 1, wherein the display is further configured to display a pointer movable in accordance with the input unit and wherein, when the display information is displayed in the first display, the processed first part includes a second part of the display information pointed by the pointer as the instruction.

11. The apparatus according to claim 5, further comprising a second input unit configured to designate a range of measurement on the medical image, and wherein the first part includes a measurement result of the range of measurement.

12. The apparatus according to claim 11, wherein the range is a distance.

13. The apparatus according to claim 11, wherein the range is an area.

14. The apparatus according to claim 11, wherein the range is an angle.

15. The apparatus according to claim 5, further comprising a second input unit configured to designate a range of measurement on the medical image, and wherein the first part includes the range of measurement.

16. The apparatus according to claim 1, further comprising a memory configured to store a table relating a first item with its plurality of detailed items of the display information as a group, and where in the first part includes the plurality of detailed items related with the first item determined by the instruction.

17. The apparatus according to claim 5, wherein the first display is further configured to display a report including information resulting from a measurement on the medical image and wherein the first part includes a second part of the information included in the report.

18. The apparatus according to claim 1, further comprising a memory configured to store a table relating a first item with one or more second items of the display information, and wherein the first display is further configured to display whether to select the first item or not and wherein, when the first item is selected by the instruction, the second items are processed as the first part by the processor.

19. The apparatus according to claim 1, wherein the emphasized manner is accomplished in color.

20. The apparatus according to claim 1, wherein the emphasized manner is accomplished in a character font.

21. The apparatus according to claim 1, wherein the emphasized manner is accomplished in a character style.

22. The apparatus according to claim 1, wherein the emphasized manner is accomplished in a boldface.

23. The apparatus according to claim 1, wherein the emphasized manner is accomplished by highlighting the first part.

24. The apparatus according to claim 1, wherein the emphasized manner is accomplished by displaying the others of the display information in a tinted manner.

25. The apparatus according to claim 1, wherein the emphasized manner is accomplished by blinking the first part.

26. The apparatus according to claim 1, wherein the emphasized manner is accomplished by adding another information to the first part.

27. The apparatus according to claim 1, wherein the emphasized manner is accomplished by underlining the first part.

28. The apparatus according to claim 1, wherein the emphasized manner is accomplished in a character size.

29. The apparatus according to claim 1, wherein the emphasized manner is accomplished in a line type.

30. The apparatus according to claim 5, wherein the first display is further configured to display a menu list of annotation information given for the medical image as the display information and the first part of the display information includes the display information selected in the menu list of the annotation information.

31. The apparatus according to claim 5, wherein the first part includes a second part of annotation information given for the medical image as the display information.

32. The apparatus according to claim 5, wherein the first display is further configured to display a menu list of body marks given for the medical image as the display information and the first part of the display information includes the display information selected in the menu list of the body marks.

33. The apparatus according to claim 32, further comprising a second input unit configured to input a second instruction for selecting a second part of the body marks from the menu list, and a second display configured to display the second part and the medical image in accordance with the second instruction, and wherein, when the second part includes the first part of the display information, the first part is displayed in the second display in a differentiable manner.

34. The apparatus according to claim 1, wherein, when the first part includes a first piece and a second piece of the display information, the first piece is displayed in a emphasized manner from the second piece.

35. The apparatus according to claim 1, further comprising a varying unit configured to vary a degree of emphasizing for the display of the first part.

36. The apparatus according to claim 1, further comprising a transmitter configured to transmit the first part and the others of the display information to an external equipment through a network.

37. The apparatus according to claim 1, wherein the apparatus is an ultrasound diagnosis apparatus.

38. A medical information processing apparatus for processing medical information regarding a plurality of measurement parameters generated in a medical imaging equipment, the apparatus comprising:

a receiver configured to receive the medical information;

a plurality of input units including a measurement parameter selection menu screen, a keyboard, and a track ball operated by a user and configured to selectively input an instruction for selecting measurement parameters among the plurality of measurement parameters to be displayed in an emphasized manner on a processed medical image;

a plurality of scan converters configured to execute measuring processes and to output mapped signals based on the instruction associated with the selected measurement parameters;

a plurality of interfaces including a video interface configured to output the mapped signals to a monitor, a printer interface configured to output the mapped signals to a printer, and a network interface configured to output the mapped signals to a remote medical imaging apparatus through a network;

a first setting unit configured to set a first part of display information among medical information of the selected measurement parameters to be displayed in the emphasized manner from non-selected measurement parameters, and to output the first part and other display information; and a processor configured to generate a graphical user interface that includes a plurality of body symbols that depict a position and direction of a probe of the medical imaging apparatus on a human body, wherein the graphical user interface allows a user to select one of the body symbols, and at least one of the body symbols is displayed in an emphasized manner;

a display controller configured to automatically display the first part of the display information of the selected measurement parameters in the emphasized manner on a first display of the processed medical image, different than the measurement parameters selection menu, and on a second display of another image, subsequent to the first display of the processed medical image, without reselecting measurement parameters to be emphasized such that the selected measurement parameter is always displayed in the emphasized manner whenever the display controller causes the processed medical image or the another image to be displayed on or printed by either one or more of the monitor, the printer, and the remote medical imaging apparatus which are selected by the plurality of interfaces, wherein the one of the body symbols selected by the user is displayed on the processed medical image.

39. The apparatus according to claim 38, wherein the apparatus is incorporated in the medical imaging equipment.

40. The apparatus according to claim 38, further comprising a transmitter configured to transmit the first part and the other display information to an external display equipment.

41. The apparatus according to claim 38, further comprising a display configured to display the output first part and the output other display information.

42. A method of processing medical information regarding a plurality of measurement parameters generated in a medical imaging equipment, the method comprising:
  receiving an instruction input by a user selectively through a plurality of input units including a measurement parameters selection menu screen, a keyboard, and a track ball for inputting the instruction that selects measurement parameters among the plurality of measurement parameters to be displayed in an emphasized manner on a processed medical image;
  executing, with a plurality of scan converters, measuring processes and outputting mapped signals based on the instruction associated with the selected measurement parameters;
  selectively outputting the mapped signals with a plurality of interfaces including a video interface that outputs the mapped signals to a monitor, a printer interface that outputs the mapped signals to a printer, and a network interface that outputs the mapped signals to a remote medical imaging apparatus through a network;
  setting a first part of display information among medical information of the selected measurement parameters to be displayed in the emphasized manner from non-selected measurement parameters;
  generating a graphical user interface that includes a plurality of body symbols that depict a position and direction of a probe of the medical imaging apparatus on a human body, wherein at least one of the body symbols is displayed in an emphasized manner;
  receiving, through the graphical user interface, a user selection of one of the body symbols; and
  automatically displaying the first part of the display information of the selected measurement parameters in the emphasized manner on a first display of the processed medical image, different than the measurement parameters selection menu, and on a second display of another image, subsequent to the first display of the processed medical image, without reselecting measurement parameters to be emphasized such that the selected measurement parameter is always displayed in the emphasized manner whenever the display controller causes the processed medical image or the another image to be displayed on or printed by either one or more of the monitor, the printer, and the remote medical imaging apparatus which are selected by the plurality of interfaces, wherein the one of the body symbols selected by the user is displayed on the processed medical image.

43. A non-transitory computer readable storage product on which is stored a computer program for processing medical information regarding a plurality of measurement parameters generated in a medical imaging equipment, the computer program having instructions, which when executed, perform steps comprising: determining an instruction input by a user selectively through a measurement parameters selection menu screen, a keyboard, and a track ball for inputting the instruction that selects measurement parameters among the plurality of measurement parameters to be displayed in an emphasized manner on a processed medical image; and executing, with a plurality of scan converters, measuring processes and outputting mapped signals based on the instruction associated with the selected measurement parameters; selectively outputting the mapped signals with a plurality of interfaces including a video interface that outputs the mapped signals to a monitor, a printer interface that outputs the mapped signals to a printer, and a network interface that outputs the mapped signals to a remote medical imaging apparatus through a network; setting a first part of display information among medical information of the selected measurement parameters to be displayed in the emphasized manner from non-selected measurement parameters; generating a graphical user interface that includes a plurality of body symbols that depict a position and direction of a probe of the medical imaging apparatus on a human body, wherein at least one of the body symbols is displayed in an emphasized manner; receiving, through the graphical user interface, a user selection of one of the body symbols; and automatically displaying the first part of the display information of the selected measurement parameters in the emphasized manner on a first display of the processed medical image, different than the measurement parameters selection menu, and on a second display of another image, subsequent to the first display of the processed medical image, without reselecting measurement parameters to be emphasized such that the selected measurement parameter is always displayed in the emphasized manner whenever the display controller causes the processed medical image or the another image to be displayed on or printed by either one or more of the monitor, the printer, and the remote medical imaging apparatus which are selected by the plurality of interfaces, wherein the one of the body symbols selected by the user is displayed on the processed medical image.

44. The apparatus according to claim 5, further comprising:
  a second processor configured to be constructed so as to execute a measurement of the medical image, wherein the input unit is constructed so as to perform an input operation by designating items of the measurement, and the first part is displayed in an emphasized manner regardless of execution of the designated items of the measurement.

* * * * *